United States Patent
Wolf et al.

(10) Patent No.: US 11,817,200 B2
(45) Date of Patent: Nov. 14, 2023

(54) GENERATING PERSONALIZED FOOD GUIDANCE USING PREDICTED FOOD RESPONSES

(71) Applicant: Zoe Limited, London (GB)

(72) Inventors: Jonathan Thomas Wolf, London (GB); Richard James Davies, London (GB); Elco Bakker, Surrey (GB)

(73) Assignee: Zoe Limited, London (GB)

( * ) Notice: Subject to any disclaimer, the term of this patent is extended or adjusted under 35 U.S.C. 154(b) by 0 days.

(21) Appl. No.: 16/985,108

(22) Filed: Aug. 4, 2020

(65) Prior Publication Data

US 2021/0065873 A1 Mar. 4, 2021

Related U.S. Application Data

(60) Provisional application No. 62/893,057, filed on Aug. 28, 2019.

(51) Int. Cl.
*G16H 20/60* (2018.01)
*G16H 40/63* (2018.01)

(52) U.S. Cl.
CPC ............. *G16H 20/60* (2018.01); *G16H 40/63* (2018.01)

(58) Field of Classification Search
CPC .................................................... G16H 20/60

USPC ......................................................... 705/2, 3
See application file for complete search history.

(56) References Cited

U.S. PATENT DOCUMENTS

| 2011/0318717 | A1* | 12/2011 | Adamowicz | G16H 20/60 434/127 |
| 2016/0232311 | A1* | 8/2016 | Segal | G16H 10/60 |
| 2018/0233223 | A1* | 8/2018 | Solari | G16H 20/60 |
| 2019/0251861 | A1 | 8/2019 | Wolf et al. | |

OTHER PUBLICATIONS

The PCT Search Report and Written Opinion dated Nov. 18, 2020 for PCT Application No. PCT/IB2020/058077, 9 pages.

* cited by examiner

*Primary Examiner* — Joshua B Blanchette
(74) *Attorney, Agent, or Firm* — Lee & Hayes, P.C.

(57) ABSTRACT

Techniques are disclosed herein for generating personalized food guidance using predicted food responses. Using the technologies described herein, instead of providing food guidance that is generalized for a group of individuals, personalized food guidance is provided that takes into account an individual's personalized responses to foods, such as the individual's glucose and fat responses, the individual's micro biome, the individual's overall health, potential health risks for the individual, and/or other data associated with the individual. Providing an individual with personalized food guidance can make choosing food easier and healthier.

28 Claims, 22 Drawing Sheets

So your scores can vary significantly from your friends

Something as common as a banana can have very different scores for different people.

Ranging from 24 to 54 – it can be an occasional treat for some while a regular food for others.

Understanding your body's response helps us generate a score just for you.

We all respond to food differently

650 — Avocados
100 Enjoy freely

652 —
- Blood sugar stress — None
- Blood fats stress — Excellent
- Gut health impact — Excellent 654 — Benefits for you — less info

- Quality of fats — Excellent
  Given that you are able to handle fats well this is an excellent choice for you. This can be a great energy source for you.

- Fibre quantity — Excellent
  Fiber is great for your gut.

- Processing level — Unprocessed
  Unprocessed food is great for your gut and free from additives.

| Net Carbs | Fats | Protein | Fibre |
|---|---|---|---|
| 1.1 g | 9.2 g | 1.2 g | 4.2 g |

*values per 100 kCal

FIG. 6H

656 → 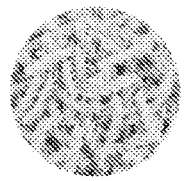 Pasta, cooked

Enjoy regularly

658 →
- Blood sugar stress — Good
- Blood fats stress — None
- Gut health impact — Bad 660 → Benefits for you          less info ∧

⚙ Quality of carbs          Good
Given that you are able to handle carbs well this is a good choice for you. It will release energy slowly and keep you fuller for longer.

○ Protein level          Good
Including protein in a healthy meal helps to control hunger.

Weaknesses for you          less info ∧

◇ Fibre quantity          Poor
Little fiber benefit for your gut

| Net Carbs | Fats | Protein | Fibre |
|---|---|---|---|
| 18.4 g | 0.6 g | 3.7 g | 1.1 g |

*values per 100 kCal

FIG. 6I

GENERATING PERSONALIZED FOOD GUIDANCE USING PREDICTED FOOD RESPONSES

CROSS-REFERENCE TO RELATED APPLICATIONS

This application claims priority to U.S. Provisional Patent Application No. 62,893,057 entitled "Methods for Improving BioMarker Predictions and Personalized Meal Recommendations," filed Aug. 28, 2019, which is incorporated herein by reference in its entirety.

BACKGROUND

Determining healthy food choices for an individual can be challenging. Not only do individuals have a large variety of food choices, but food that is healthy for one individual may not be healthy for another individual. Age, sex, weight, the microbiome of an individual, as well as other factors affect what foods an individual should select to eat. For example, while low carbohydrate food or low-fat food may be beneficial for one individual, that same low carbohydrate or low-fat food choice may not be beneficial for another individual. In many cases, an individual may try many different types of foods and nutritional plans in an attempt to find the nutritional plan and foods that work best for them. Providing guidance about what to eat and how to change their diet can be very difficult and confusing for an individual given the plethora of food choices and the complex nature of the responses the individual has to different foods.

BRIEF DESCRIPTION OF THE DRAWINGS

FIGS. 6A-6M illustrate exemplary UIs for providing personalized food guidance and scores.

DETAILED DESCRIPTION

Figure 1:
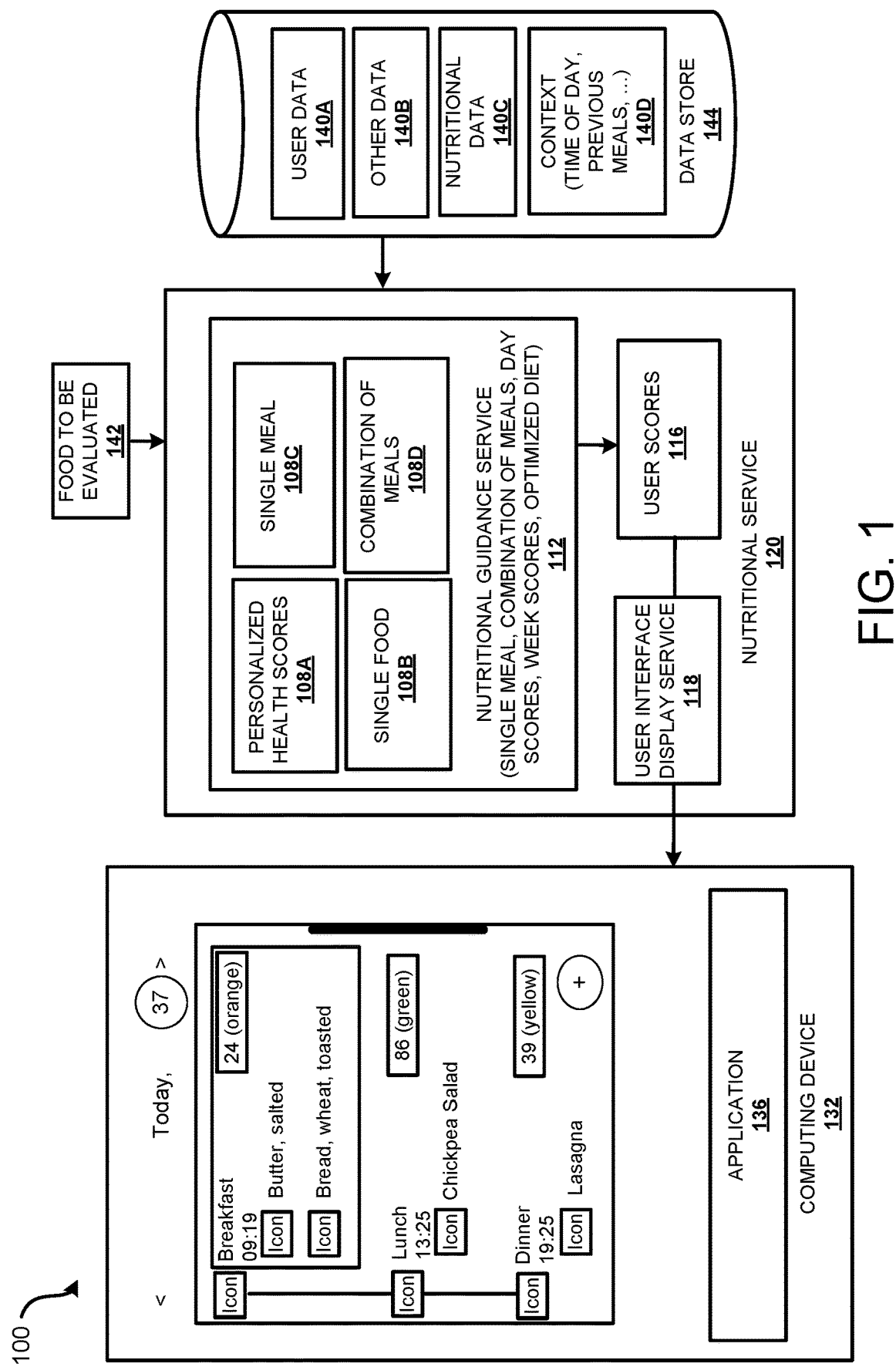
FIG. 1 is a block diagram depicting an illustrative operating environment in which personalized food guidance is generated using predicted food responses.

The following detailed description is directed to technologies for generating personalized food guidance using predicted food responses. Using technologies described herein, instead of providing food guidance that is generalized for a group of individuals, personalized food guidance is provided that takes into account an individual's personalized responses to foods, such as the individual's glucose and fat responses, the individual's microbiome, the individual's overall health, potential health risks for the individual, and/or other data associated with the individual. Providing an individual with personalized food guidance can make choosing food easier and healthier, and help them to understand how to improve their existing diet.

According to some examples, the personalized food guidance may include guidance data such as but not limited to personalized health scores (e.g., glucose, fat, . . . ), guidance/recommendations on food that has not yet been eaten, and/or other guidance data (e.g., via a User Interface (UI)) on food/meal(s) that have already been eaten). The guidance data may be used by an individual to help them understand how they can improve their diet. For instance, a user may receive guidance data by viewing a UI on a mobile device, or some other device, to readily determine how good/bad a particular food/meal is for them before they eat the food, how a particular food/meal was for them, how a particular food/meal is affected by food(s) already eaten by the user, and the like. The guidance data may also indicate a score, or some other indicator, that summarizes information about how the user has eaten over a particular time period (e.g., a day, a week, and the like).

In some configurations, the user is presented with UI elements that classify the scores similarly to how traffic lights depict the state of traffic. Generally, the traffic light UI elements, as explained in more detail below, convey information to a user about frequency and quantity as well as relative quality. As an example, a "green" UI element may indicate that a food/meal is considered healthy for that individual and may be eaten frequently, "yellow" may indicate that the food/meal is less healthy and to proceed with caution, and "red" may indicate that the food/meal/score is unhealthy for that individual and should be eaten rarely and in small quantities. As an example, an apple for one user may be a 9/10 and be shown as "green", whereas chocolate may be scored for that user as a 6/10 and be displayed as "yellow". In some configurations, there may be four or more traffic light colours. In some configurations, the shade of the color may change to indicate subclassifications within a particular level (e.g., a brighter green for more healthy, and less bright shades of green for less healthy but still within the healthy range).

Similarly, the UI elements may be used to represent a score for a combination of meals over a time period, which may be a day or a week in some examples. For instance, a "green" indicator for two or more combined meals may indicate that the user ate healthy for the day, whereas "yellow" or "red" may indicate that the user could improve upon their food choices. In other examples the food/meal score may be used to rank food and display it in some other way (for example in categories like "healthier", "medium", "less healthy"). In some examples the meal score will reflect the overall predicted effect that this meal will have on the individual's metabolism and provides a means for individuals to compare different meals.

According to some examples, the color (or some other indicator) associated with the UI element is based on one or more personalized scores generated by a nutritional service. For instance, a score may be shown as green if the score is above some threshold, a score for a particular user may be shown as red if below a certain threshold, and a score may be yellow if the score is between red and green. In other examples, the UI elements may be displayed differently (e.g., other colors, different shapes to represent different scores, and the like.) In some configurations, additional information may be provided to the user. For instance, a message may be provided to the user to explain the impact of previous foods/meals or exercise may have on a particular score that is displayed.

To generate personalized food guidance, a "nutritional service" produces personalized score(s) for one or more personalized health scores, and/or foods/meals that is based on personalized data about an individual and the individual's biological responses to the particular food/meals. The personalized data may include data that predicts how one or more of the individual's biomarkers will change postprandially, data that predicts an individual's potential risks such as diabetes or cardiovascular disease, as well other data associated with the individual.

When comparing two foods, it is often not immediately obvious which food is better, as one food may lead to a better response in one biomarker (for example blood sugar), while another may lead to a better response in another biomarker (eg blood fat). A nutritional service may calculate the relative importance of the different responses for that individual and show a simple score and/or traffic light to allow an individual to easily compare any two meals or understand how they could improve their diet.

The nutritional service may combine multiple data sources about the individual's response to each food in such a way that the nutritional service takes into account the individual's own personalized risks, so as to optimize the overall meal score for each individual based upon their own body's responses. As discussed briefly above, the nutritional service may present the generated scores using a "traffic light system" to convey information about frequency and quantity as well as relative quality, and it may generate other messaging for example to explain the impact of previous meals or exercise on the score that is displayed.

In some examples, the nutritional service may use one or more other services, to score the individual's responses to food on more than one dimension (e.g., the impact of the food on biomarkers such as glucose, triglycerides, insulin, energy and hunger and its impact on shifting the microbiome towards a specific goal). In some cases, these scores may depend on factors that change rapidly such as the time of day, what was eaten previously or the amount of sleep.

The nutritional service may also use other data when generating the scores for a particular food. For instance, the nutritional service may use properties of the food that can be measured independently of the user, such as grams of fiber, level of food processing, type of fiber, glycemic index, sugar content, salt content, alcohol content, whether the food is fermented, whether the food is a high polyphenol food such as dark chocolate or vegetables, whether the food is meat, the composition and source of fat in the food, the composition of the fibre in the food, the production method, preparation methods applied by the user (such as cooking method), the inclusion of particular ingredients such as (but not limited to) flavour enhancers or emulsifiers, the method by which the food was preserved, the location where the food was produced, the method by which animals contributing to the product were reared, caught or slaughtered, and the like. The nutritional service may weight these properties differently depending upon the individual (for example people with high lipid responses may be guided more strongly against alcohol and in favour of fibre) In some configurations, the nutritional service may generate different scores that are combined to generate a single overall rating, which may be referred to as a "meal score" of the food in a particular context.

As such, using the techniques described herein, rather than a user having to compare lots of different scores for each food (as happens today using the nutritional information found on food labels), the single meal(s) score may make it easier for an individual to choose the right food at a particular moment or to understand the quality of historical food choices. In addition, a personalized meal score reflecting an individual's personal responses may be more valuable than generic food label data that does not change if an individual has a risk of diabetes or cardiovascular disease. For example, comparing two or more foods may be very difficult for a user when the different foods may cause different biomarkers to go in opposite directions when the different foods are eaten by the user. For instance, does the user choose the food which improves their fat response or does the user choose the other food that improves glucose response? As another example, is a particular fruit good for a particular user when it leads to a high glucose response, but that fruit is high in fiber that will improve the user's gut health? Using the food guidance and viewing the UI elements presented to the user that indicate the different generated scores makes it easy for a user to determine what foods to eat as well as how well the user has eaten. In some examples, the nutritional service may also use food/meal scores to rank a list of foods or to generate a suggested diet plan which consists of a set of foods chosen to be optimal for the individual when combined. In some cases, these foods will also incorporate the individual's food preferences such as being vegan or not liking tomatoes. More details relating to generating personalized food recommendations are described below with reference to FIGS. 1-10.

FIG. 1 is a block diagram depicting an illustrative operating environment 100 in which personalized food guidance is generated using predicted food responses. As illustrated, environment 100 includes a nutritional service 120, a nutritional guidance service 112, a UI display service 118, a data store 144, and a computing device 132.

As illustrated in FIG. 1, the operating environment 100 includes one or more computing devices 132 in communication with a nutritional service 120. In some examples, the environment 100 may be associated with and/or implemented by resources provided by a service provider network such as provided by a cloud computing company. The environment 100 may include a collection of computing resources (e.g., computing devices such as servers). The computing resources may include a number of computing, networking and storage devices in communication with one another. In some examples, the computing resources may correspond to physical computing devices and/or virtual computing devices implemented by one or more physical computing devices.

The data store 144 may include a variety of data 140. In some configurations, an individual may generate and provide data 140 using a variety of at home biological collection devices, which collect a biological sample which requires a biological assay to be performed to generate electronic data 140. Some of the data 140 may be biomarker data, such as blood glucose results collected by a CGM, as well as other types of data. Some of this data may be non-biomarker data such as photos, time stamps, as well as other data associated with a user or group of users.

Some of this data 140 may be nutritional data associated with individual foods, 140C. In some configurations this may include data from nutritional databases such as fiber or grams of sugar. Some of this data may come from individuals who have recorded eating such food and shared their own biological responses to this food such as blood glucose responses or reported hunger. By aggregating this data and using other information about these individuals, in some configurations some of the nutritional data for this food such as its impact on blood sugar can be calculated.

An individual may also provide data 140 using computing device 132. In some configurations an individual can input data 140 into one or more software applications 136. For example, an individual may enter the food they consumed, a value indicated by a measurement device, their waist measurement, and the like. Alternatively, and/or in addition to the above, data 140 generated by other measurements can be used to assist in determining when a food was eaten, and/or a test was performed. For example, in some cases a CGM can be used to confirm the start point of a meal. In this example, data recorded by an individual about when they started to eat can be verified by confirming that there is a rise in glucose detected by the CGM, provided there was sufficient carbohydrate in the meal. More details on the type of data that may be included in data store 144 is presented with the description of FIG. 2.

The nutritional service 120 can access the data 140 when generating the personalized nutritional guidance and/or scores for a particular user. In some examples, the nutritional service 120 utilizes both data associated with the user providing the data and data from other users performing similar tests. In other examples, the data utilized is associated only with the user. According to some examples, the data 140 can include data obtained from a clinical setting, which is typically more accurate than at home measurements.

In some examples, the nutritional service 120 may utilize one or more machine learning mechanisms. For example, the nutritional service 120 can use a classifier to classify the data within a classification category. In other examples, the nutritional service 120 may generate one or more scores using one or more machine learning mechanisms.

As briefly discussed above, the nutritional service 120 generates personalized food guidance using predicted food responses. Instead of providing a user, such as a user of computing device 132 with food guidance that is generalized for a group of individuals, the nutritional service 120 generates personalized food guidance that takes into account the user's responses to foods, such as the individual's glucose and fat responses, the individual's microbiome, the individual's overall health, potential health risks for the individual, and/or other user data 140A that is associated with the individual.

According to some configurations, the nutritional service 120 uses a nutritional guidance service 112 to generate a variety of personalized food guidance data that may be provided to a user via UI 134, or through some other mechanism. The personalized food guidance data may include data such as but not limited to personalized health scores (e.g., glucose, fat, . . . ) 108A, guidance/recommendations/scores on single food items (already eaten or not yet eaten) 108B, single meals (already eaten or not yet eaten) 108C, combination of meals (already eaten or not yet eaten) 108D, and/or other guidance data (not shown).

In some examples, the nutritional guidance service 112 provides the guidance data to a user interface display service 118 to provide to the user via UI 134. The guidance data displayed in UI 134 may be used by an individual to help them understand how they can improve their diet. For instance, a user may receive guidance data by viewing UI 134 on a mobile device, or some other device, to readily determine how good/bad a particular food/meal is for them. In the current example illustrated in FIG. 1, instead of just showing the user what they have eaten and possibly data about the calories consumed or other data obtained from a food label, the nutritional guidance service 112 generates scores for each meal and the combination of the meals for the data. As illustrated, the UI 134 shows an overall score for the day "37", a score of "24" for breakfast, a score of "86" for lunch, and a score of "39" for dinner. More examples are provided with regard to FIGS. 6A-6M.

As briefly discussed above, in some examples, the UI elements displayed within the UI 134 classify the scores into a smaller number of categories. For example, in FIG. 1, the scores may be presented with a color to indicate how "healthy" a particular food, meal or combination of meals is for a user. In the current example, the lunch score of "86" is shown as a "green" UI element that indicates that it would be healthy to eat large quantities of that lunch frequently for that individual. The dinner score of "39" is shown as a "yellow" UI element and indicates that the food/meal is less healthy and should be eaten in moderate quantities about once a week, and breakfast is displayed as "orange" to indicate that breakfast should be eaten rarely or in small quantities. As will be discussed in more detail below, the foods eaten earlier by an individual may impact the scores for food eaten later in the day. Stated another way, the same meal eaten at different times may be scored differently for the same user depending on what foods the user has eaten before that meal.

As such, using the techniques described herein, rather than a user having to compare lots of different scores for each food (as happens today using the nutritional information found on food labels), the single meal(s) score may make it easier for an individual to choose the right food at a particular moment. In addition, a personalized meal score reflecting an individual's personal responses may be more valuable than generic food label data that does not change if an individual has a risk of diabetes or cardiovascular disease. For example, comparing two or more foods may be very difficult for a user when the different foods may cause different scores can be difficult as different biomarkers may go in opposite directions when the different foods are eaten by the user. For instance, does the user choose the food which improves their fat response or does the use choose the other food that improves glucose response? As another example, is fruit good for a particular user when it leads to a high glucose response, but the fruit is high in fiber that will improve the user's gut health? Using the food guidance and viewing the UI elements presented to the user that indicate the different generated scores makes it easy for a user to determine what foods to eat as well as how well the user has eaten. In some examples, the nutritional service may also use food/meal scores to rank a list of foods or to generate a suggested diet plan which consists of a set of foods chosen to be optimal for the individual when combined. In some cases, these foods will also incorporate the individual's food preferences such as being vegan or not liking tomatoes.

Figure 2:
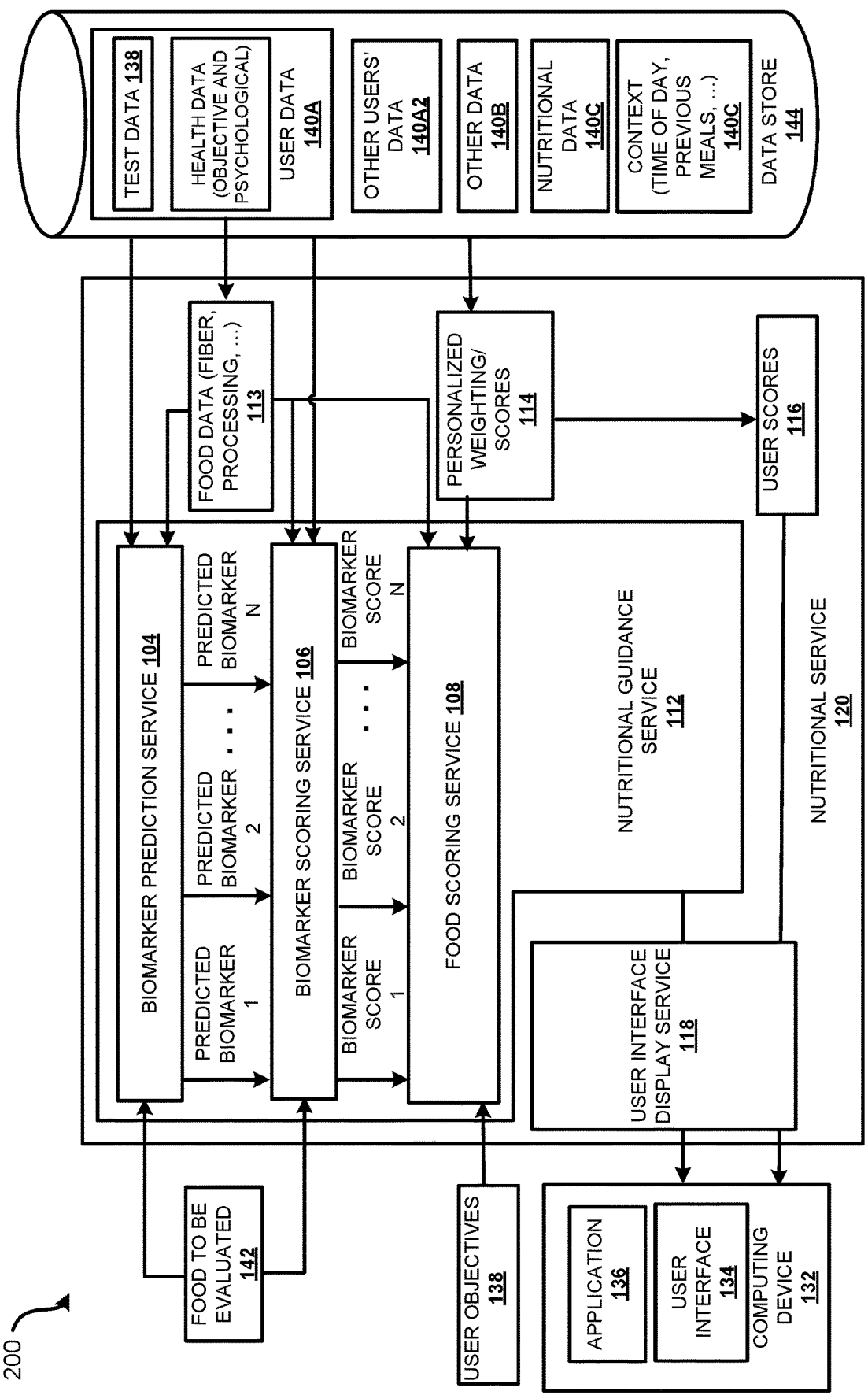
FIG. 2 is a block diagram depicting an illustrative operating environment in which personalized food guidance is generated using predicted food responses.

FIG. 2 is a block diagram depicting an illustrative operating environment 200 in which personalized food guidance is generated using predicted food responses. As illustrated, environment 200 includes more details as compared to environment 100. For example, environment 200 includes biomarker prediction service 104, biomarker scoring service 106, food scoring service 108 as part of the nutritional guidance service 112. In other configurations, the services may be located in different environments and/or locations.

In some examples, the nutritional guidance service 112 may receive a single input (e.g., the glucose rise linked to foods). In this example, the nutritional guidance service 112 generates a prediction of the biomarker of interest using biomarker prediction service 104 and a score for that single biomarker using the biomarker scoring service 106. However, in other examples where more than one aspect of the food is calculated, nutritional guidance service 112 predicts many different biomarkers (e.g., biomarkers 1-N) of the assessed aspects (glucose response, blood fat response, and the like), scores each biomarker change individually using the biomarker scoring service 106 and weights the scores so that the scores are comparable and then combined into a single score using food scoring service 108.

In some examples, in addition to utilizing biomarker inputs, the nutritional guidance service 112 also utilizes non-biomarker inputs such as but not limited to food data 113 such as fiber content, amount of processing on the food (e.g., high, medium, low), polyphenol content, fermentation and the like. In some examples the nutritional guidance service uses information about the individual to determine personalizing weighting 114 for combining these scores, which determine how to combine the different biomarker scores 106 and food data, 113 into a single score.

The biomarker prediction service 104 generates a prediction of the postprandial response of the user's biomarker to the food being evaluated. The biomarker scoring service 106 generates scores that are personalized for a particular user. The scores generated by the biomarker scoring service 106 are related to the predicted health impact of these biomarker changes on the particular user, so for example a small rise in blood fat after a meal might have no negative impact on health and so the score for blood fat might be at the best level for that meal but a large rise in blood fat 6 hours after a meal might be detrimental to health and lead to a bad score for blood fat for that meal for that person. The nutritional service 120 may then use these biomarker scores to generate food scores for one or more foods/combination of foods/meals to make individual food recommendations by generating personalized meal scores for any meal using food scoring service 108. In some examples, the food scoring service 108 uses personalized weighting/scores 114 to determine how to weight the different biomarker scores when combining them to generate a single meal score. For example, the food scoring service might need to combine a glucose score, a blood score and a gut health score, and might do so by weighting each of these scores and then combining them.

In some examples, if the personalized impact of a food is to be calculated by using predictions of the glucose and triglycerides levels after eating that food combined with the food's impact on the microbiome for that individual, generating a meal score by the food scoring service 108 may consist of using the personalized weighting/scores to combine all three of these scores. The nutritional service 120 is designed to do this such that it recommends the best possible food for the individual based upon the inputs provided. In other examples the nutritional service 120 will use information beyond biomarker predictions as inputs into its biomarker scoring, for example it may take into account family health history, measures of blood chemistry taken in a fasting state such as baseline glucose or triglycerides, or measures of blood chemistry that do not change postprandially such as cholesterol or HbA1c. The nutritional service 120 can also utilize one or more data analysts, machine learning, and/or some other mechanism to generate a quality score for the data.

Figure 3:
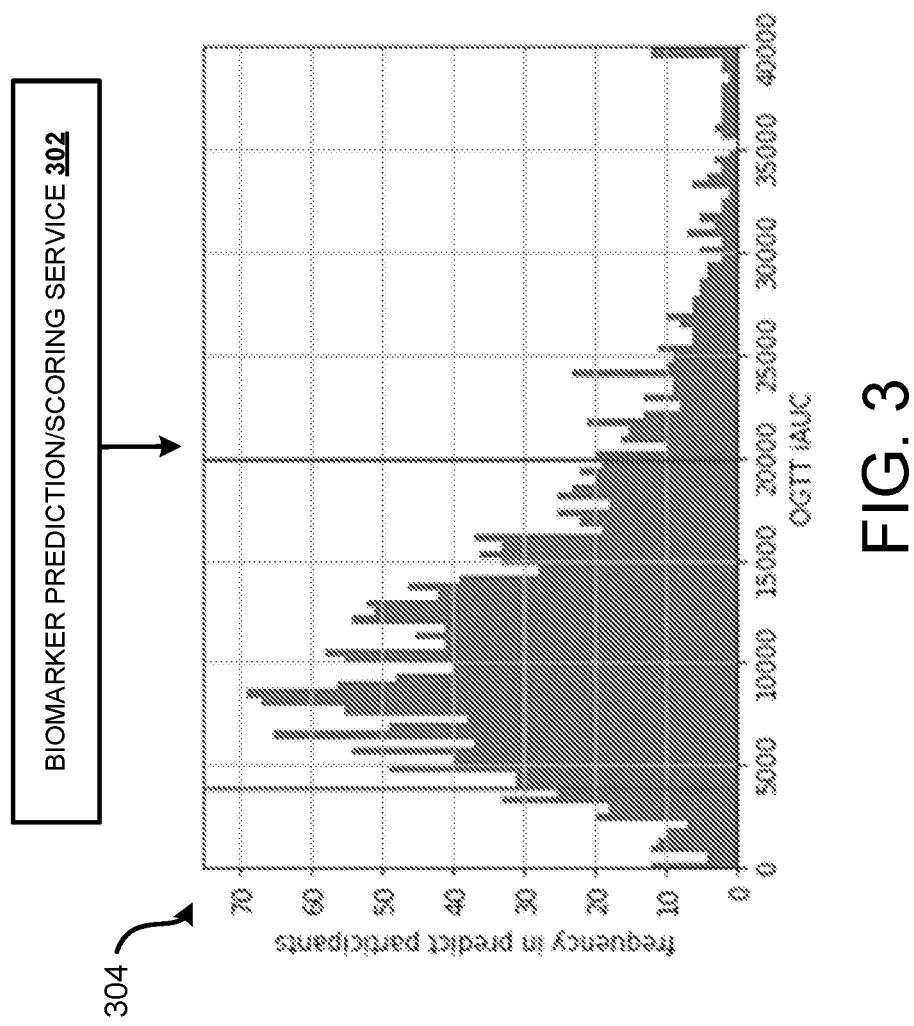
FIG. 3 shows predicting a biomarker using a biomarker prediction service/scoring, service.

FIG. 3 shows predicting a biomarker 304 using a biomarker prediction service/scoring service 302. As discussed above, a biomarker scoring service 106 scores predicted biomarkers obtained from biomarker prediction service 104. As illustrated, the prediction service/scoring service 302 is a combination of the biomarker scoring service 106 that scores predicted biomarkers and the biomarker prediction service 104.

In some examples, the prediction service/scoring service 302 may combine postprandial and static elements to generate a score. This score generated by the prediction service/scoring service 302 is designed to reflect how good or bad the biomarker response is biologically for a particular user. In some examples the score may evaluate the predicted rise in glucose or triglycerides after a meal or may evaluate the increased likelihood of snacking due to hunger. According to some examples, the biomarker prediction service/scoring service 302 compares a large sample of biomarker responses for the same meal. For example, using this data on blood glucose responses to an Oral Glucose Tolerance Test (OGTT) meal, the blood glucose response for a given individual may be scored based on its deviation from sample average for the OGTT meal. The graph in FIG. 3 shows how such a blood glucose response could be calculated for an individual within 1,100 individuals in the PREDICT study using responses to a standardized OGTT test. In some examples, the individual's deviation from the average may be used as an input into the personalized weighting for that biomarker, 114

The biomarker prediction service/scoring service 302 may use different approaches when scoring a biomarker response. In some examples, the biomarker prediction service/scoring service 302 may score a biomarker response based on the deviation of the score from the population average for biomarker response to the same meal. In other examples, the biomarker prediction service/scoring service 302 may score a biomarker response based on a combination of the response and factors relating to the user such as the user's pre-existing risk to negative health outcomes related to that biomarker (for example, scoring a person's blood triglycerides response based on the predicted triglycerides rise for a meal and the person's risk for cardiovascular disease based on 10 year ASCVD (acute coronary syndromes, myocardial infarction, stable or unstable angina, arterial revascularization, stroke/transient ischemic attack, peripheral arterial disease) risk score, Framingham risk score (10-year cardiovascular risk of an individual), or similar risk score).

In other examples, the biomarker prediction service/scoring service 302 may score a biomarker response based on epidemiological assessment of the risk increase associated with the same or similar biomarker measured in similar conditions. For example, scoring the postprandial triglycerides rise based on an epidemiological assessment of the risk associated with postprandial triglycerides measurements from the Nurses' Health Study. As briefly discussed above, the biomarker prediction service/scoring service 302 may combine factors related to person and the predicted biomarker response.

The biomarker prediction service/scoring service 302 may also score a biomarker based on epidemiological dietary data and a large sample of predicted biomarkers responses for meals associated with that diet. For example, making postprandial triglycerides predictions for the meals eaten by participants in the PREDIMED (Primary Prevention of Cardiovascular Disease with a Mediterranean Diet) study and scoring a triglycerides response by the association between the predicted triglycerides response for these PREDIMED participants and the incidence of negative health outcomes for these study groups). This, again, could combine factors related to a person and the predicted biomarker response.

After generating the biomarker score, the biomarker score may then be provided to a food scoring service 108 as illustrated in FIGS. 1 and 2. This biomarker score may be weighted according to weights 114 associated with a particular individual to score the meal. In some examples, the biomarker score may aggregate a number of other biomarkers, for example there may be an "aggregate harmful lipid marker" which may be calculated by the biomarker prediction service/scoring service 302, or some other component, by combining a number of biomarkers that might be measured using a metabolite screen, at a particular time (fasting, or at a set time point after a challenge meal or meals).

Figure 4:
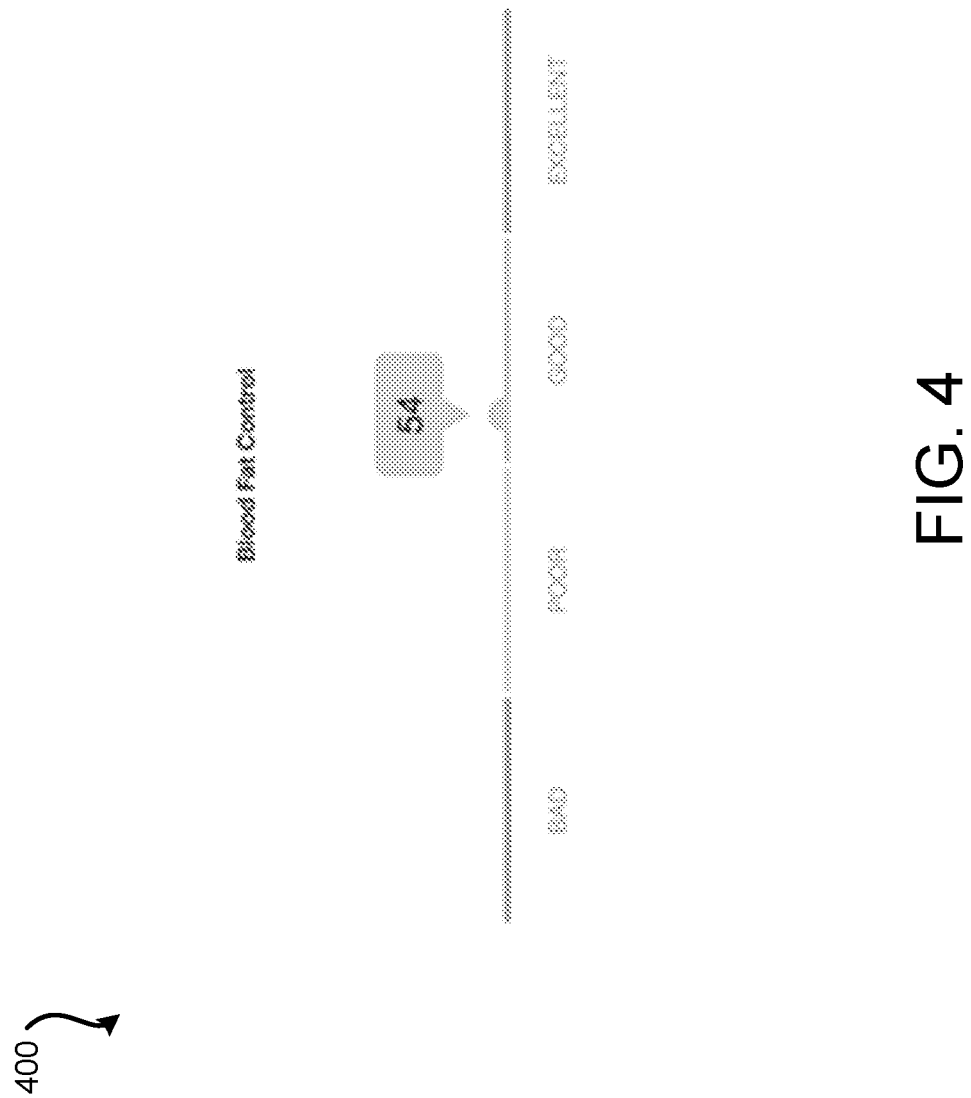
FIG. 4 illustrates a personalized score relating to blood fat control for a particular user.
Figure 5:
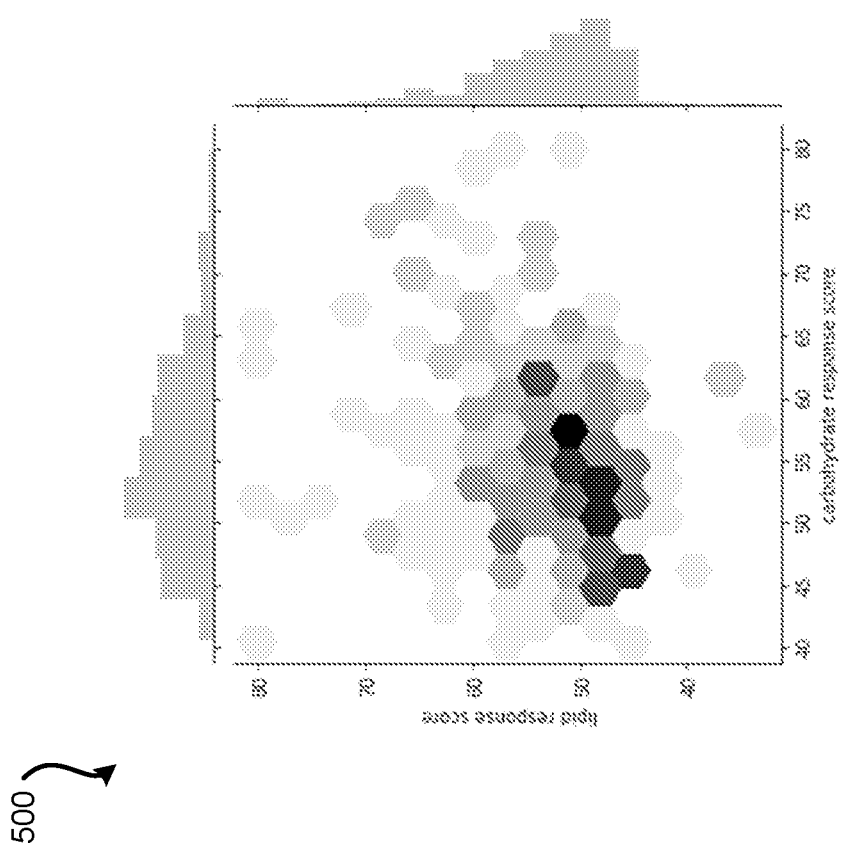
FIG. 5 illustrates a plot where an individual is placed within a full spectrum of individuals across two axes, such as for example carbohydrate and lipid response.

FIG. 4 illustrates a personalized score relating to blood fat control for a particular user. As discussed above, the nutritional service 120 may be configured to generate different scores that are associated with a particular user. In the example of FIG. 4, the nutritional service 120 has generated a blood fat control score of "54" for a particular user placing that user within a "good" category compared to many other users. In some configurations, the scores may be presented within a UI, such as UI 134. According to some examples, a personalized health score may be calculated by weighting one or more responses.

In some examples, an individual's glycemic and lipemic responses may be tested by eating one or more standardized meals for example and by measuring their glucose iAUC using a continuous glucose monitor, and their lipemic response by measuring the changes in their triglycerides after the standardized meal. These two measures are used to calculate health scores for fat (lipid) response and carbohydrate response (blood sugar control), by comparing this individual's responses with the responses of a large number of other users who have taken the test.

The nutritional service 120 may also provide other personalized health scores 108A such as but not limited to metabolic risk, carbohydrate response, blood sugar control, lipid response, microbiome health, and the like. According to some examples, the user's personalized health scores are calculated by using the user's measured biological data compared with data from a large set of others so that the nutritional service 120 may determine where to place the user's score on a scale. The chart in FIG. 3 shows an example of doing this by measuring a user's response to a carbohydrate heavy meal compared to 1,100 other people eating the same meal during the PREDICT study.

For example, knowing from epidemiological studies that high postprandial glycemic responses are associated with negative health outcomes, the nutritional service 120 can compare a person's postprandial glycetnic response to a standardized meal with those of a representative population. In so doing, the nutritional service 120 can determine if the user's response is particularly high, and thereby identify that the user should adjust their lifestyle to avoid negative health outcomes.

In some configurations, the nutritional service 120 combines a measured postprandial response with a variety of risk indicators, such as fasted blood glucose or family history to provide an overall measure of the risk for a user. Using measured biological responses and known or inferred relationships between those biological responses, lifestyle and negative outcomes (chronic diseases, weight gain, low subjective energy levels etc.) the nutritional service 120 can provide both an overall assessment of the user's propensity to negative outcomes and the way in which that propensity can be influenced by their lifestyle choices. The inference of novel relationships is facilitated by the large data set of user information collected, either by expert inspection and/or statistical analysis. This can be via simple scores informed by expert input or via more sophisticated statistical analysis.

In some configurations, the nutritional service 120 may adjust the personalized health score for other factors beyond those measured with a single response. For example, a lipid response score can combine measured postprandial response (for example the rise above fasting of their 6 hour Triglycerides), with ASCVD risk (risk of cardiovascular disease) and familial history of cardiovascular disease, so that the biomarker score generated by the nutritional service 104 can be adjusted for known future risks for one individual compared to another when calculating that individual's score for a particular lipid response. For example, even with the same predicted biomarker response after a meal, an individual with a high risk might have a much more negative score than someone with a low risk. As another example, the personalized health score for a user's carbohydrate response (glucose) score can be calculated by the nutritional service 120 by combining a user's blood sugar response to carbohydrates, measured by means of the 2 h postprandial glucose response above fasting level to test meals; and a user's risk of developing problems in their glucose metabolism, measured by their fasted glucose levels, and family history of diabetes. In some other examples, a carbohydrate response score can be calculated by the nutritional service 120 in this way, but also adjusted to a lower score if the individual has high fasting lipid levels as high fasting lipid levels are known to be a marker of difficulty managing high postprandial glucose responses.

In some configurations, the scoring service 108A may generate different personalized health scores for each user (e.g., lipid response score, carbohydrate response score, microbiome health score). In some examples, the scores may be between 0 and 100, where 0 is best and 100 is worst. These scores may be used as input for the personalized weighting 114 and/or the food scoring performed by the food scoring service 108, as well as being displayed to the user through user interface 134 to help guide them better on how to adjust their diet.

These personalized health scores can also be used to explain simply the results of complex tests. These scores may be used by a viewer to easily see how they are doing compared to others. In other examples, the scores may be presented using some other display, such as the hexagon plot shown by indicator 500 of FIG. 5. Indicator 500 shows a plot where an individual is placed within a full spectrum of all individuals across two axes, such as for example carbohydrate and lipid response. The score on each axis can then be used as parameters for the personalized scoring system of the nutritional service 120 to adjust average food scores for that individual, as part of the personalized weighting 114.

In some examples, the meal weighting takes the individual's health scores for different responses (for example carbohydrates, blood fat, insulin) and uses these to compare them with standardized individuals with defined weightings for all biomarkers 106 and food data 113 (for example from expert input). By comparing with these standardized individuals, a personalized weighting can be calculated for any individual, 114 to allow the different biomarkers to be combined by the food scoring service 108. Using the scoring system as described herein, two individuals who might have exactly the same predicted biomarker responses to the same meal will receive different meal scores. For example, if one user is at risk of diabetes and the other is not then a meal with a higher glycemic response may be given a worse score for the first user than for the second despite having the same predicted glucose iAUC.

The personalized health scores generated by the nutritional service can also be used to explain an individual's sensitivity to certain elements of food. By applying the Personalized Health Scores to a standardized meal or a set of meals, the resultant person scores reflect an overall or average response of this individual to changes in a particular input or biomarker. In one example, the personalized health score for glucose might represent that person's sensitivity to carbohydrates, measured by means of the 2 h postprandial glucose iAUC responses above fasting level to test meals. The personalized score for fat might represent that person's sensitivity to fats. In other cases, a personalized health score might also include other inputs such as the individual's familial or DNA generated risks of a certain disease which is known to be linked to certain biomarker changes such as peaks in glucose or fats. By sending these personalized health scores to a UI display service 118, the scores can be displayed directly to the individual who can therefore understand better their responses to food and why the nutritional services is making the recommendations that it does.

Generating personalized weighting/scores for different biomarkers in a scientifically informed manner can be challenging, given limited data on how to compare risks associated with different biomarker responses or different foods. According to some configurations, expert dietary input is combined with biomarker predictions to help define the personalized weighting/scores service, 114. In some examples, dietary recommendations are obtained from experts in the field for a range of users with a state of health recognizable to the experts. For example: person A may be high BMI, prediabetic, age 55-65 etc., whereas person B may be aged 30-45, frequent jogger, eats largely a plant based diet. These recommendations could be of various forms such as "Person A should be strongly discouraged from eating processed meat", or "For Person B, the scores for low Glycemic Index carbs should be higher than those for good quality fats". After obtaining the recommendations from the experts, the biomarker prediction service generates biomarkers for the participants/foods for which we have statements and machine learning may then be used to generate the personalized weighting/scores for each biomarker 106 and food data 113 that maximally satisfy the statements of the experts. Through this approach the food scoring service can generate food scores for any food and any individual, where the guidance can be personalized both to the individual's different biomarker responses and to the individual's health risks, and allows the combination of different biomarkers into a single score, solving for the problem of dealing with comparing foods where some biomarkers improve and some get worse.

Figure 6A:
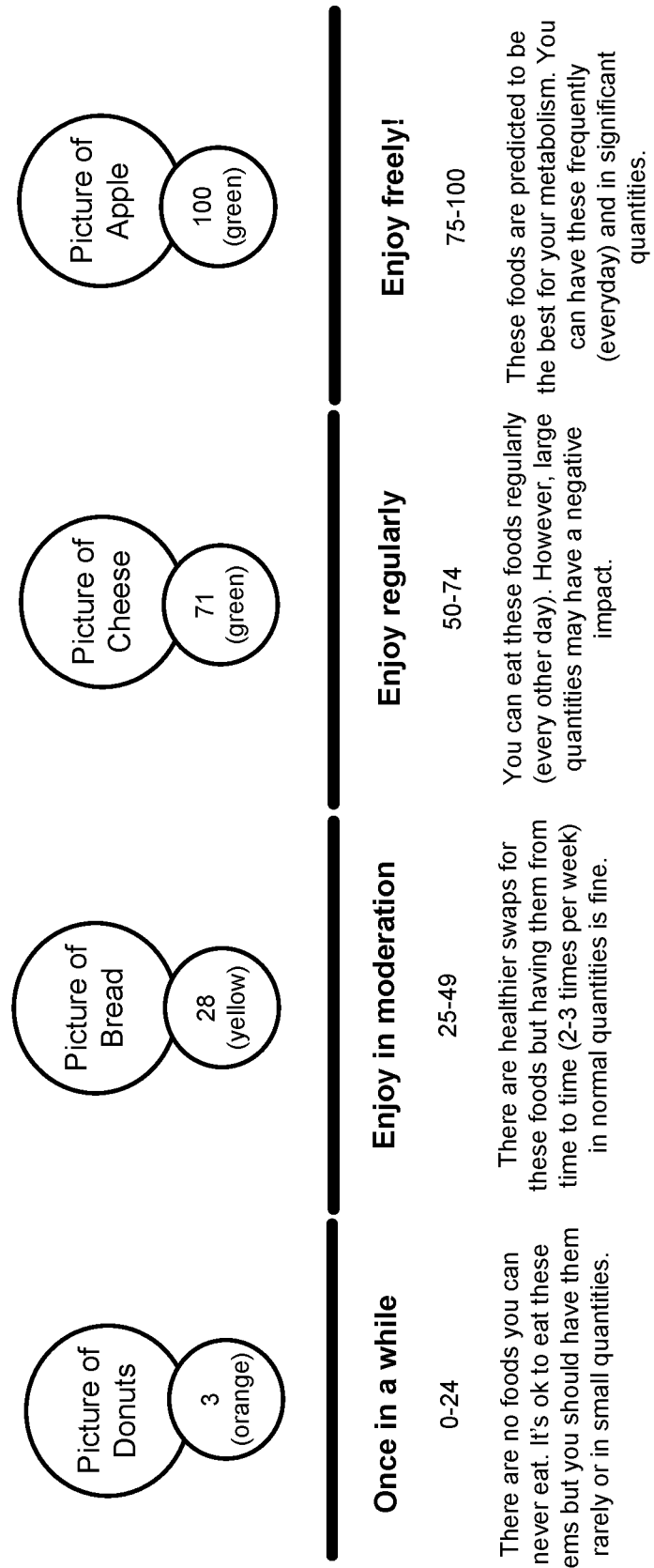

FIG. 6A illustrates an exemplary UI showing personalized scores for different foods. As illustrated, FIG. 6A shows four different foods each of which falls into one of the 4 traffic light zones used to indicate how "healthy" a particular food is for a user. In other examples, the indicators could be for fewer categories, such as two (eat regularly/eat rarely), three (enjoy freely/eat regularly/eat rarely or in small quantities), and the like.

Presenting scores using the UI elements as described herein has many advantages. For example, the traffic light display of scores provides a non-arbitrary basis for deciding what range of scores to give to foods. When comparing two individuals with different personalized scores without the traffic light system it is unclear whether everyone should have their food rank 1-100 (where arbitrarily 100 is best and 1 worst), or whether someone with worse responses should have scores between 1-25, and someone healthier can have scores between 1-100. The traffic light system determining quantity and frequency allows a user both to understand the relative ranking of food and the quantities associated with it. At the same time, by keeping a score as well as a traffic light color it allows the user to see small differences between foods that are both within the same traffic light "bucket", and so improve their diet by shifting to higher scoring foods within the traffic light "bucket" and understand what the overall score of a meal will be when combining multiple foods.

The traffic light system also provides guidance on frequency to users, i.e., how often a food should be eaten. For example, glucose response can vary 10× between healthy individuals. Without traffic lights, if scores were only based on an individual's glucose response and were calculated based on the absolute glucose response, then the healthiest individuals might see even coca cola score 90%, while those with the worst glucose response might see even lentils score 10%. Such scores do not align with the results of epidemiological evidence, or any nutritional advice. Instead these traffic lights provide guidance to ensure that even those with diabetes or hyperlipidemia are provided with food that they can always eat, while even those who are currently very healthy (so all their biomarker responses look good compared to most of the population) are guided that certain foods should only be eaten rarely or in small quantities.

In phrasing the categories in terms of actionable statements—the frequency with which the food should be consumed—the scores described above can be given interpretable meaning and guide the user towards a diet that is thought to be healthful. It also guides the user on the frequency with which they can eat less healthy food, allowing a more manageable diet since it need not say never eat those foods.

The functional categorization of foods into traffic light categories can be delivered as part of the weighting service described above. Expert input on the appropriate traffic light for a set of foods and a set of individuals can be gathered, and therefore these form part of the optimization that the system must solve for. As a result some examples might ensure that there are always some starches that can be eaten frequently, or that low GI vegetables are always scored so they can be eaten as frequently as desired.

Figure 6B:
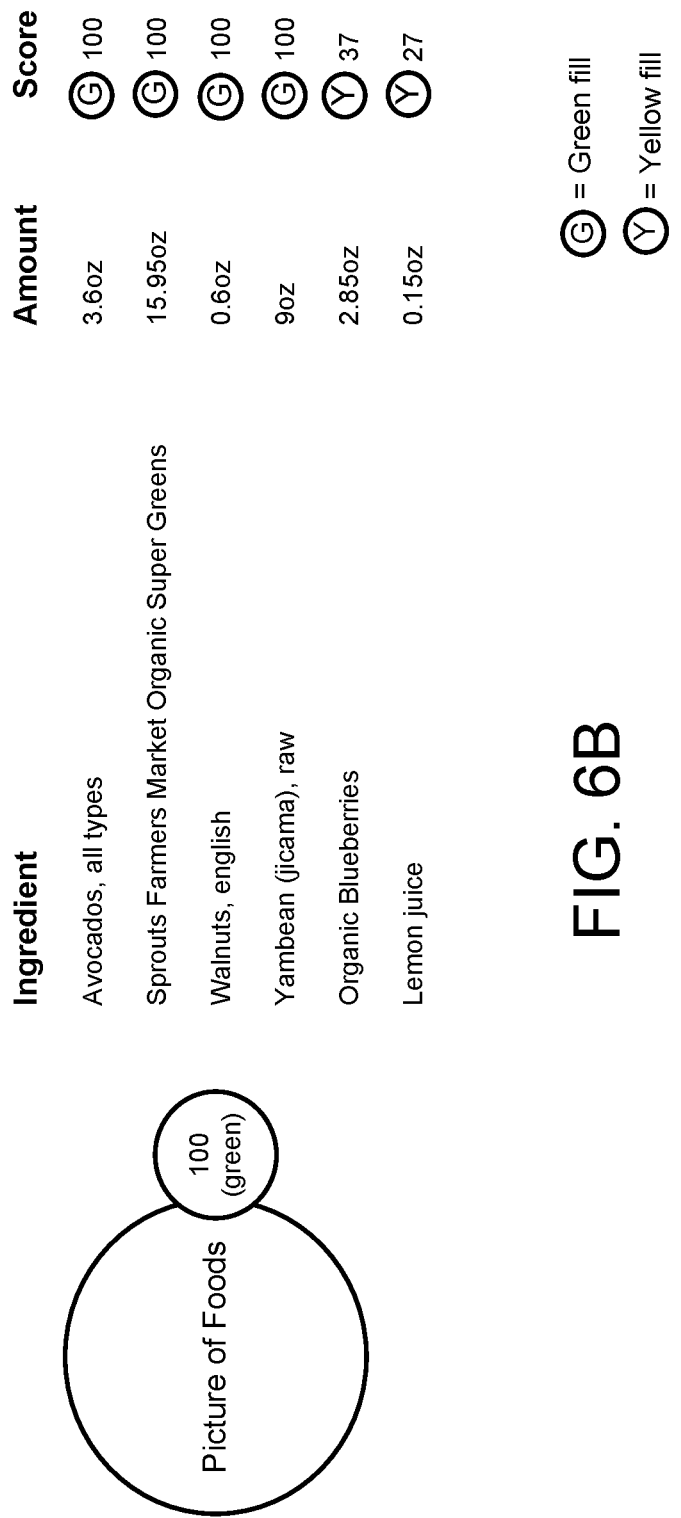

FIG. 6B shows the effects of adding more food to a meal. Adding different food can change the overall score of a meal. In the example of FIG. 6B the meal with blueberries started at 37, and when the other listed foods were added the score moved to 100. Under calorie counting approaches, it is not possible to improve a meal by adding more food to the meal as this always increases the total calories in the meal which is bad. In the example of FIG. 6B each food item in a meal has a score, while the overall meal may have a score which is different from all its components as it is calculated using the nutritional service 112 which may not be linear in how biomarkers are scored or combined.

FIG. 6B also illustrates a scoring of individual ingredients that are included in a breakfast. Because the scoring system combines biomarkers and food data, it is able to use the same approach to score multiple foods in a meal as a single food—so for example it can calculate the total triglycerides rise and glucose iAUC from eating five foods in a meal, as well as the total fibre. Using the same techniques described herein for individual foods, the nutritional service 120 calculates scores in real-time for any combination of foods in any quantities, while still ranking meals by relative quality and mapping them to the traffic light UI elements that correspond to the score. The nutritional service may use scores that change in a non-linear fashion as different foods are combined, and as the size of the meals increases. For example, there may be no negative impact of eating fats below a certain level, but a negative impact once this level is passed. In some examples, the scoring system is designed to be independent of calories, so that 100 calories of sugar and 200 calories of sugar will score the same, either within certain ranges of calories or certain ranges of biomarker responses. Such a scoring system also allows meals with different calories to be directly compared. For example, 100 calories of coca cola might score worse than 300 calories of almonds, which is different from a calorie based system.

Day or week scores are an extension of meal scores that summarize the overall meal quality over this time period, so as to help guide the user on how to improve their diet.

Day scores are not simply the addition of individual meals (as calorie counting would do) but can combine multiple meals scored using the nutritional service 120 and generate an overall day or week score which is itself also displayed using the traffic light UI elements. This overall score can be used to identify the overall quality of that day or week's food. Additionally, the day scores can adjust for the diversity of meals, for sleep, exercise, stress, and the like. The day score is a variation of the calorie weighted average of meal scores for food eaten throughout the day. The variation of the day score may depend on various factors, which may include: the fat clearance capabilities of the person; how much fat was eaten throughout the day and the quality of the fat eaten; how many vegetables, fruits, high fibre, fermented and high gut score foods were eaten throughout the day, how much exercise was performed in the previous and the current day, when was the exercise done with respect to the meals (fasted, just before meal, after meal, etc.); how much sleep did the person get during the night, and the like.

While the system described encourages food quality over a focus on calorie quantity, consuming extremely large quantities of calories in a single meal may result in negative health effects. According to some examples, the meal score and/or the day score may drop as the meal passes a particular calorie threshold. According to some examples this drop occurs by comparing the harmful effects of the meal (i.e. biomarker excursions) to those of reasonably sized meals. This calorie limit can be personalized using data about the person's height, weight and activity levels and established estimates of daily calorie usage.

Figure 6C:
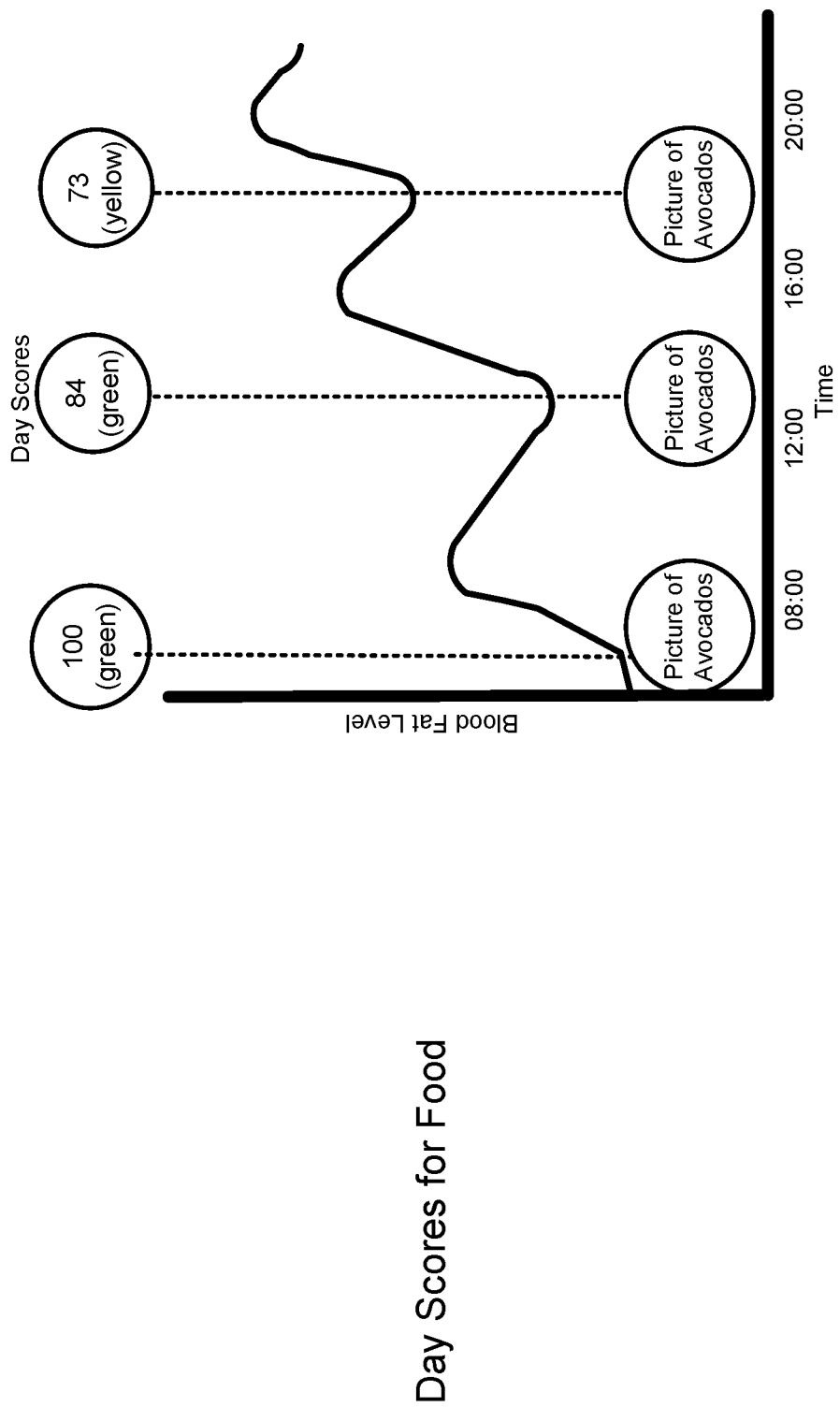

FIG. 6C illustrates an example of how a day score could be calculated at different times during a day, and how the day score can be different than the meal score even if the same meal is consumed repeatedly during the day. In this example, while the avocado meal was scored at 100, after eating it three times over a few hours it led to a much lower day score of 73 due to the impact of the fat in the previous meals leading to increased blood fat levels.

The nutritional service 120 may also generate personalized aggregate diet recommendations. Usually food recommendations either recommend individual foods (eat avocados, don't eat bacon) or give aggregate diet recommendations (e.g., Atkins diet recommends very high fat levels, low-fat diet recommends the reverse, most government guidelines recommend a narrow range of overall fat intake). The personalized nutritional service described above, which can take predictions of individual biomarker responses to nutritional inputs like carbohydrates, proteins and fat and use this to score meals can be used to predict personalized aggregate diet recommendation (that individual's "Optimal Diet"). In some examples this would predict the correct percentage of energy coming from fat, carbohydrate and protein for an individual. In other examples it would calculate how much fibre should be in their diet. In other examples it would set targets for what proportion of fat, carbohydrate and other nutrients should come from high quality dietary sources of each nutrient. These Optimal Diets would be individually personalized.

By using the meal weighting within the nutritional service 120 and inputting these person scores the nutritional service 120 may calculate an optimal carbohydrate to fat ratio in their diet, which will serve to maximize the scores from the food scoring service 108 by minimizing the harm caused from biomarker responses (e.g., excessive triglycerides or glucose responses). This ratio will be personalized and will reflect the underlying biomarker responses of the individual as well as any other risks and inputs that feed into the personalized score. Because the food score may also be affected by data about the food (e.g. fiber), in some examples this ratio may differ depending on the quality of the fats or carbohydrates being assessed.

In some examples the individual's current ratio of fat to carbohydrate may also be calculated. For example, by requesting the user to log everything they eat for a period of days. With this meal logging data, the nutrients in the foods can be determined. The ratio of nutrients such as carbohydrates to fat in the individual's habitual diet may then be calculated. In some cases, the proportion of nutrients such as carbohydrates and fats are coming from high quality dietary sources of each nutrient. By combining this data with the calculated Optimal Diet, the nutritional service 120 can offer personalized recommendations to the user on whether they should increase or reduce the amount of fat and carbohydrate in their habitual diet, as well as which specific foods are healthiest for them as they make this change A meal score may also take into account the quality of dietary sources such as fat. The meal score, as outlined above, may utilize a prediction of the level of blood fat following the meal. Where there is not enough measured data to predict the responses to individual fats this can be replaced by using categories of food where there is existing evidence (epidemiological, controlled trials or otherwise) as to the relative quality of the fat. For example, the fats in nuts and seeds are known to be healthier than the fats in processed meat such as bacon. It is also possible to categorize according to specific types of fat that are found on food labels, such as saturated, monounsaturated and polyunsaturated fats.

Having identified the nature of the fats in the meal that is to be assessed, the fat prediction may be multiplied by a coefficient X %, where X % represents the quality of these fats versus the fats in an average meal. X is determined by the expert opinion of scientific advisors based on the existing evidence. The adjusted fat prediction then enters into the meal score, and affects the food recommendations for a participant.

This approach can be extended beyond fat to apply to any food property where the prediction service lacks enough data to predict an answer based upon the existing training data. For example it can also be used to predict the gut health of foods based on properties like fiber, fermentation and polyphenols in the absence of sufficient microbiome data tracking the impact of these individual foods. In another example, it can be used to predict the glycemic response to foods using properties such as glycemic index in the absence of sufficient glycemic response data tracking the impact of these individual foods.

As discussed above, meal scores may change based on previous meals and other inputs. Historical nutritional models (e.g. calories, back of pack information or quality measures for food) assume that the meal score is only a reflection of the properties of the meal. The following describes using information from previous meals within a predefined period of time to adjust the biomarker predictions and/or the meal scores for subsequent meals. The method we describe below is for lipids, but the same approach can also be used for carbohydrates or other biomarkers.

In this example for lipids the biomarker of interest (for example postprandial elevated blood triglycerides) may be predicted by taking account of the meals eaten in the previous 6 hours (or in other examples a different amount of time) as well as this meal. The fat content of this meal, the previous meals, the source and composition of the fats, and measurements of the user's blood triglycerides response to a sequence of test meals can be used to determine what the expected elevation in blood triglycerides will be. This may then be scored based on expert or epidemiological guidance on the harmful effects of elevated blood triglycerides levels. In some examples, this prediction may use a time window specific to each individual user. In some examples, this prediction may use a weighted time window which applies different weights to previous meals according to the time point at which they were eaten during the time window. In one simple example the calculation might simply take the total grams of fat consumed over this 6 hour period and use this to provide guidance to the user.

Figure 6D:
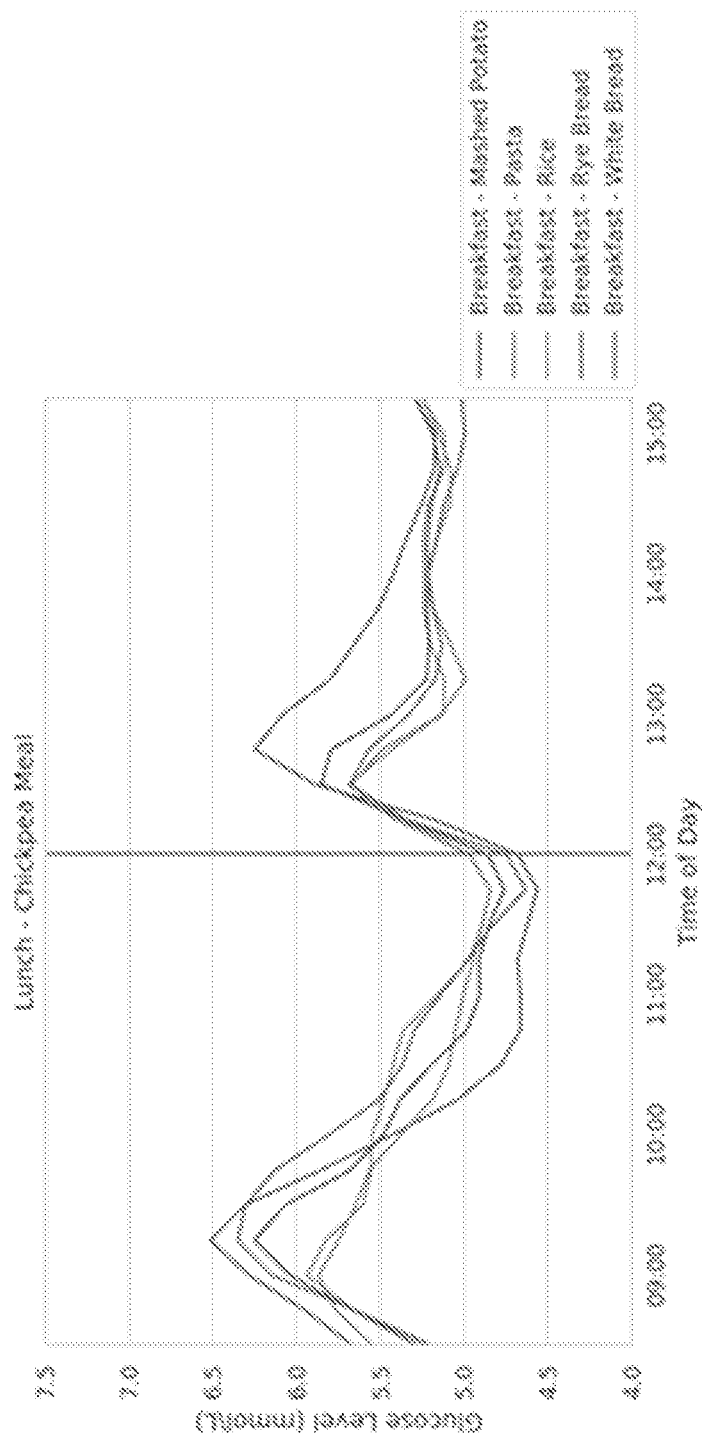
Figure 6E:
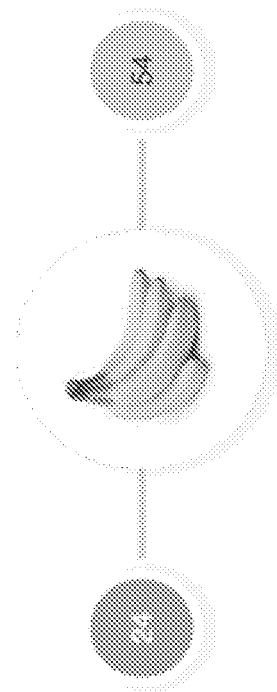
Figure 6F:
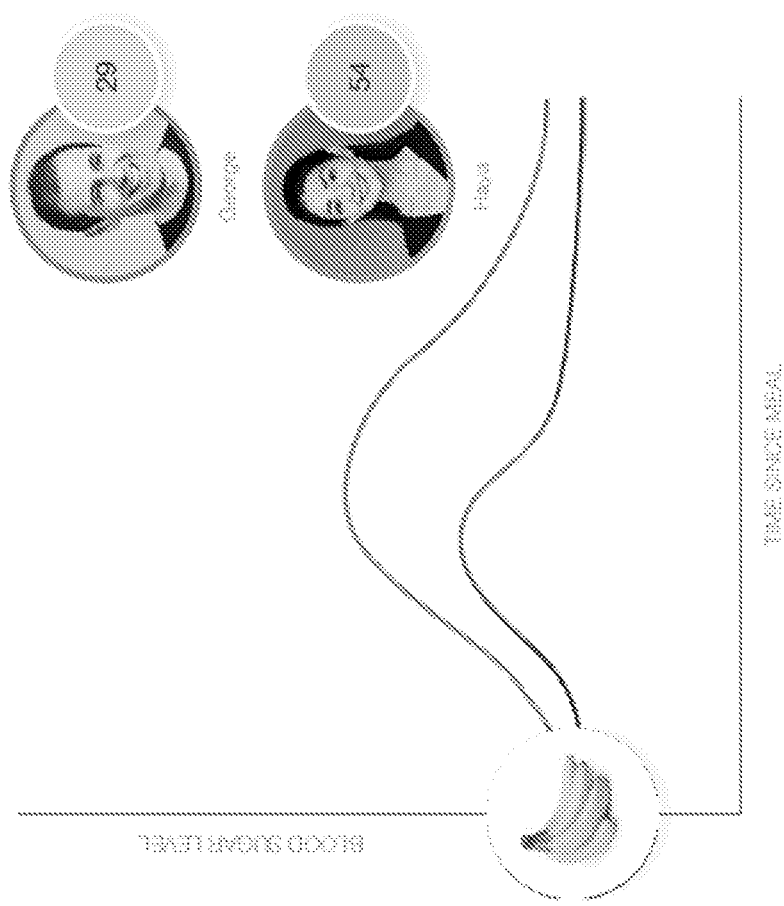
Figure 6G:
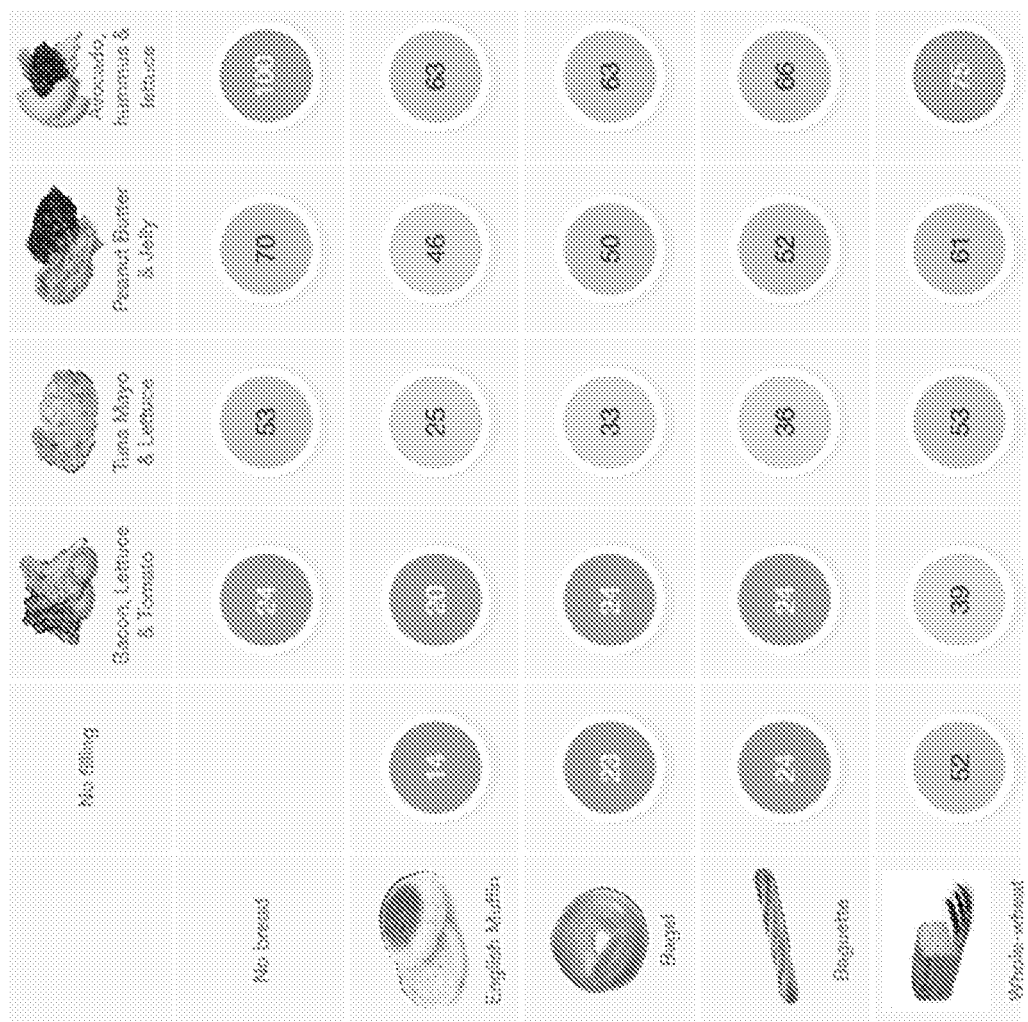
Figure 6J:
Figure 6K:
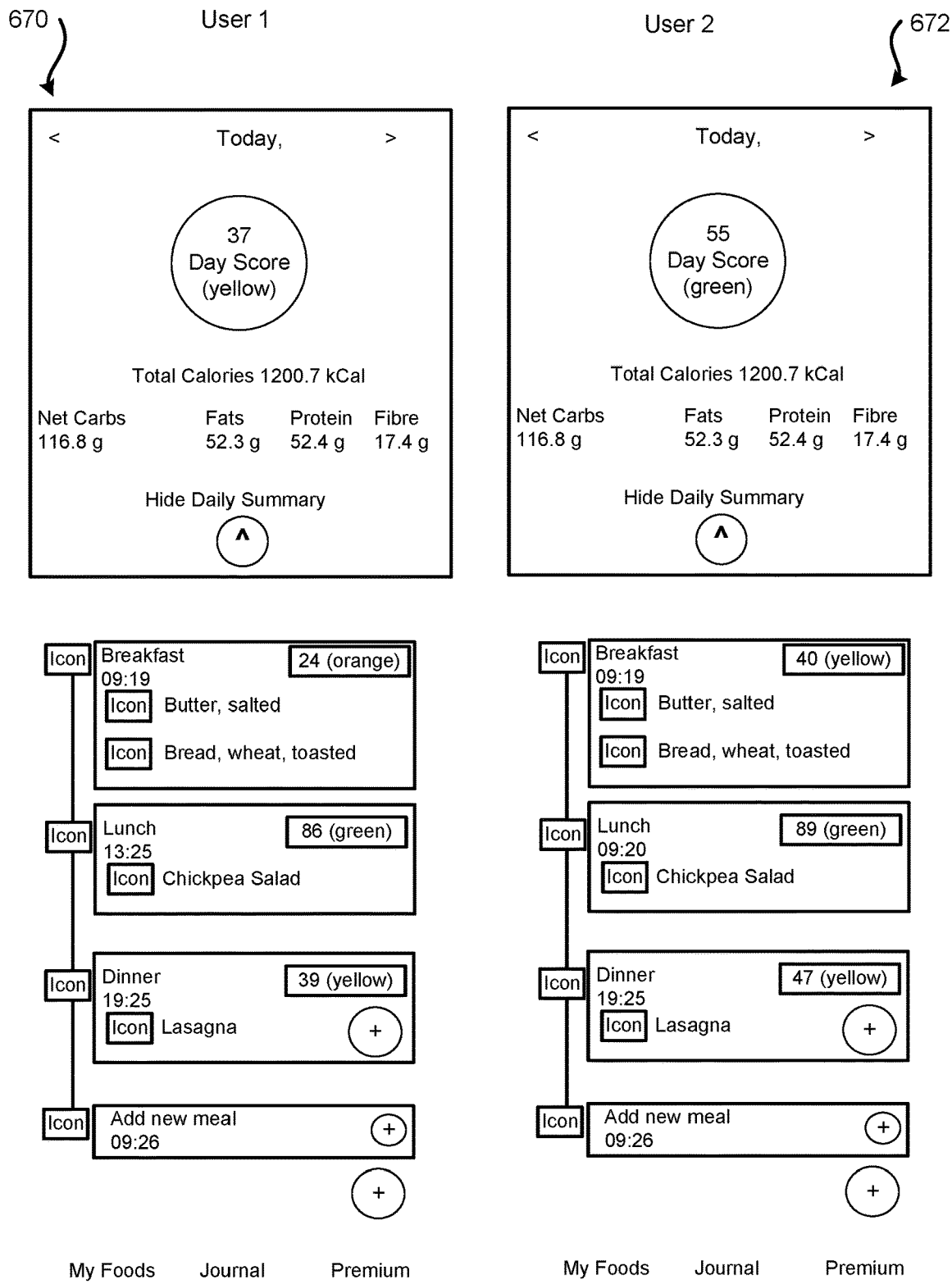
Figure 6L:
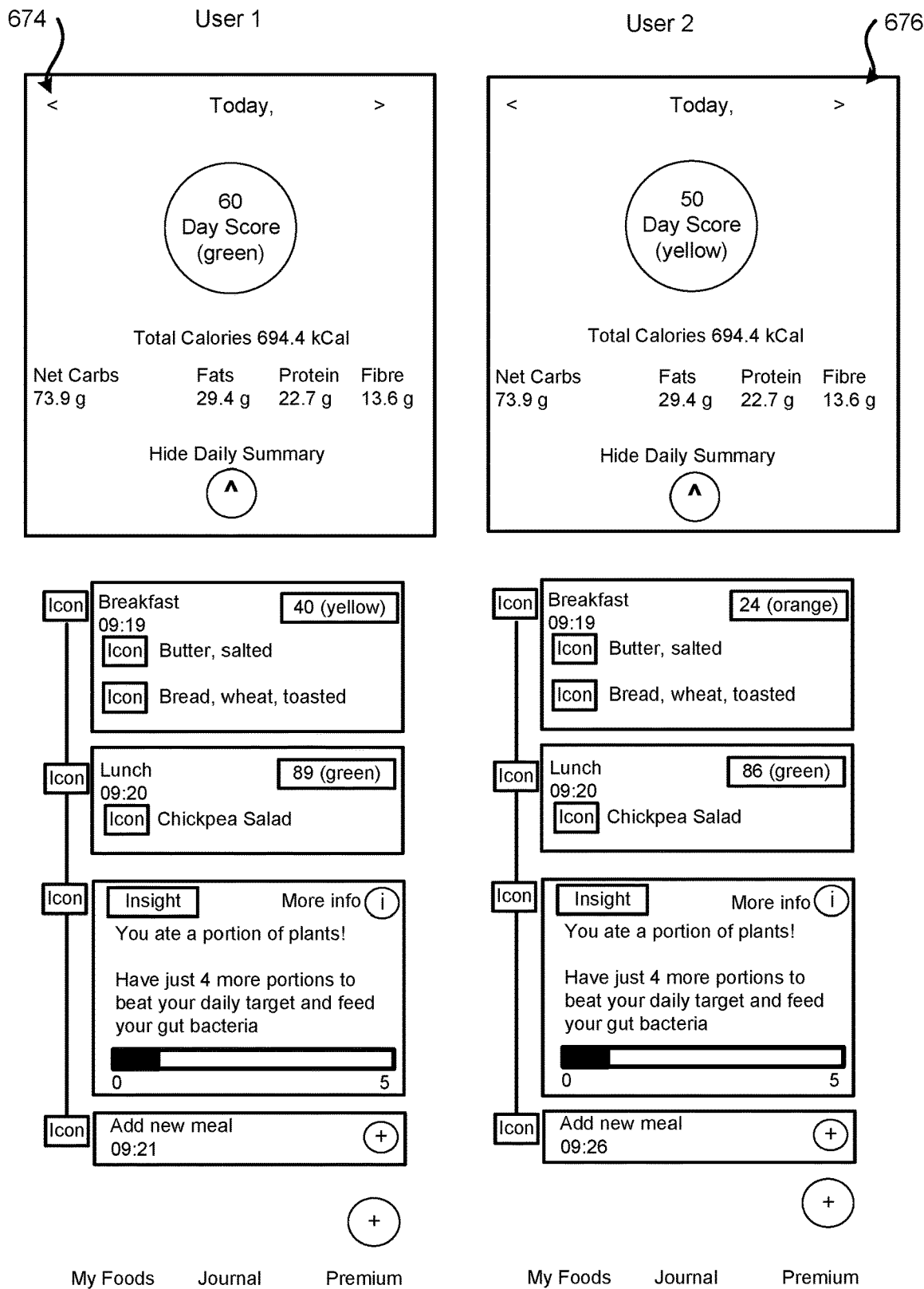
Figure 6M:
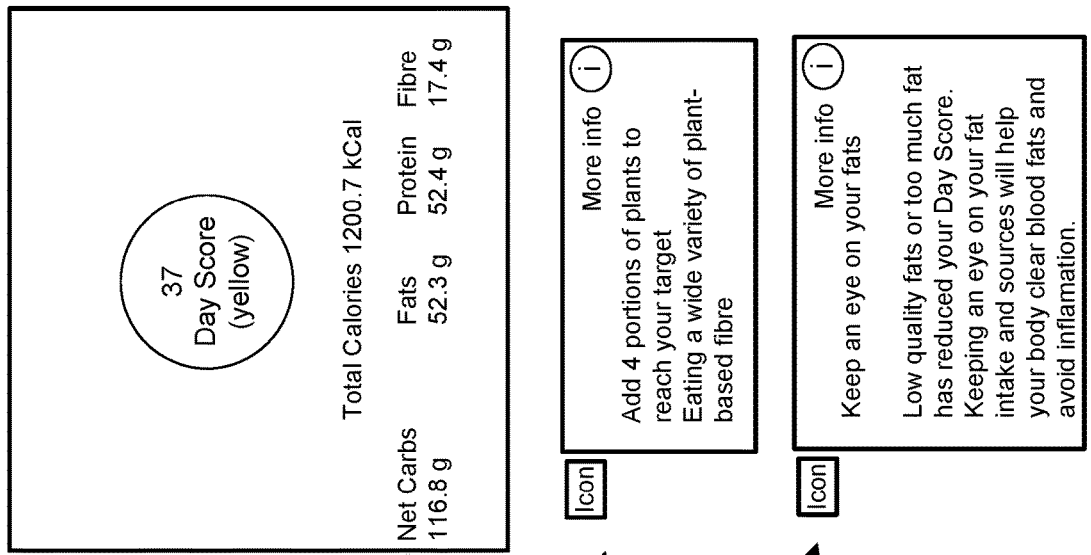
Figure 6M:
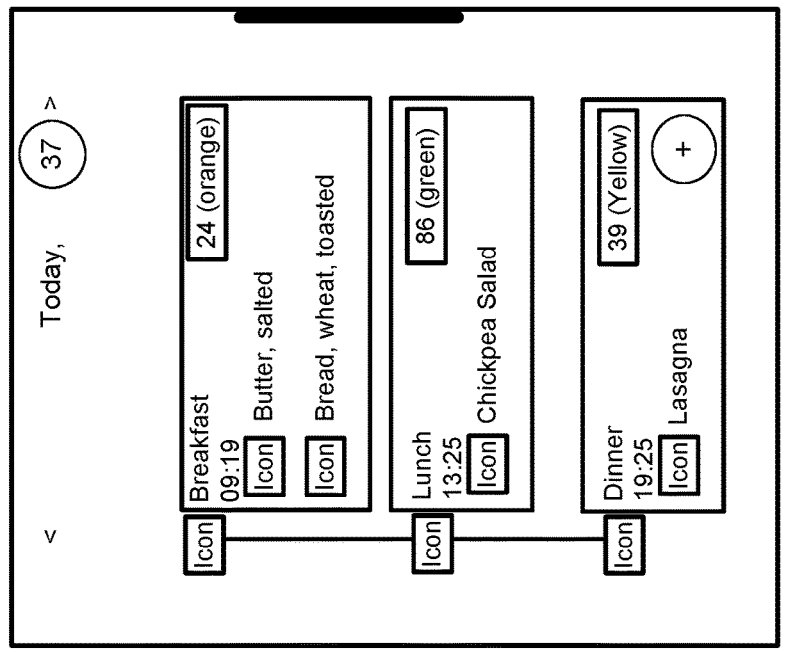

After calculating the meal score for the latest meal taking into account previous meals, the nutritional guidance service can display a message to the user explaining that the impact on the meal score or day score was from the previous meal, for example 684 in FIG. 6M.

FIG. 6D shows the variations in average blood glucose concentrations over time among users who consumed different breakfasts before having the same chickpea meal for lunch. All these breakfasts were isocaloric (around 300 calories) and were consumed around 3.5 h before lunch; however, they all lead to different blood glucose levels right before lunch and different blood glucose spikes after consuming the same lunch. This shows a similar example for carbohydrates as was previously shown for fats, so that in the same way the previous meal (breakfast) can be used to adjust the lunch carbohydrate scores conveyed to the user, and a message delivered explaining the impact of previous meals on the current meal.

Almost all research into food responses has measured responses in a fasted context and in a clinic setting. This is to try and reduce complications. However this does not reflect the vast majority of real meals which take place outside the clinic and the majority of which are eaten with less than 12 hours of fasting since the previous meals.

Glucose responses to a given lunch meal may vary substantially based upon the type of breakfast meal previously consumed. Amongst other things, the breakfast meal has an impact on: the baseline level of the lunch meal; and the iAUC, height and shape of the response to the lunch meal.

Some part of this impact may be food specific, and some may reflect broader properties of the breakfast meal (for example it may be that high glycemic index breakfasts, such as mashed potatoes, produce a bigger lunchtime glycemic response for all lunch meals.)

While FIG. 6D shows responses for glucose, this may be applied to other postprandial biomarker responses for example blood fats such as triglycerides. It is known that blood fats are affected by previous meals which is why clinical tests are carried out at fasting but it is not known how different meals affect this.

Techniques described herein measure multiple properties of the previous meal or meals and use these to predict the differences in the postprandial response for a food that is eaten non-fasted vs fasted. In some examples, these properties of the previous meal include how many hours earlier it was eaten, how many grams of fat, carbs and protein were in the meal, the composition of the meal (baked potato or spaghetti bolognese), the biomarker responses such to the previous meal. These responses are also affected by characteristics of the individual, for example their insulin sensitivity affects how the previous meal affects the current meal by influencing the levels of insulin and fat in the body.

To predict these responses, the techniques described herein may be utilized. In some examples, this means that recommendations will differ by time of day and by what you previously ate. A UI may display different recommendations and different scoring of foods based on this. For example, it may recommend a higher fat meal at breakfast than at lunch due to the impact of breakfast on fat levels at lunch, or may recommend a higher fat lunch due to the higher glucose responses it predicts at lunch from the mashed potato eaten at breakfast.

The results of this personalized diet recommendation can be improved by getting individuals to carry out standardized tests both as part of the training set data and for the individual wanting recommendations. In some examples this might involve eating a set lunch a fixed number of hours after a set breakfast to measure that individual's response to timing. In another example, this might involve eating a number of different set breakfasts and seeing how this impacts the same set lunch. In another example, this might involve eating a number of different set lunches after the same set breakfast.

As a result, this nutritional service 120 can deliver much more accurate predictions of food responses than is possible using either clinic based models or using prediction models that assume that individual "foods" or "meals" are the building blocks to predict responses rather than biomarkers that change based on previous meals FIG. 6E shows a diagram that a score for different users may vary significantly for the same food. In the current example, the score for bananas range from 24 indicating that the user may eat bananas occasionally according to traffic light UI elements, to 54 indicating that bananas may be eaten regularly by those users.

FIG. 6F shows a graph of the blood sugar level for two different users for eating bananas. As can be seen, the user that had a score of "29" for bananas has a higher blood sugar level after eating bananas as compared to the user who had a score of "54" for eating bananas.

FIG. 6G shows a diagram that illustrates food/meal scores changing based on combining foods. As illustrated it can be seen that depending on how the foods are combined, different scores are generated by the nutritional system.

FIG. 6H shows exemplary food guidance displayed within a UI. As illustrated, UI 650 shows a food score for avocados for a particular user, along with indicators 652 for "Blood sugar stress", "Blood fats stress", and "Gut Health impact." which are ways to display elements of the biomarker scoring in a way that is easy for the user to understand. As can be seen, a user may view the UI 650 and easily be able to determine impacts of eating the food. UI 654 shows a list of benefits for the user, and general nutritional information.

FIG. 6I shows exemplary food guidance displayed within a UI. As illustrated, UI 656 shows a food score for cooked pasta for a particular user, along with indicators 658 for "Blood sugar stress", "Blood fats stress", and "Gut Health impact." As can be seen, a user may view the UI 656 and easily be able to determine impacts of eating the food. Unlike the feedback for avocados as illustrated in FIG. 6H, the Blood sugar stress" is good, "Blood fats stress" is none, and "Gut Health impact" is bad for this user. UI 660 shows a list of benefits for the user, and a list of weaknesses for this particular food along with general nutritional information, which data reflects personalized responses to the food as well as standard characteristics of the food.

FIG. 6J shows exemplary food guidance displayed within a UI. As illustrated, UI 662 shows a food score for lean ground beef for a particular user, along with indicators 664 for "Blood sugar stress", "Blood fats stress", and "Gut Health impact." As can be seen, a user may view the UI 662 and easily be able to determine impacts of eating the food. Unlike the feedback for avocados as illustrated in FIG. 6H, and cooked pasta illustrated in FIG. 6I, the "Blood sugar stress" is none, "Blood fats stress" is bad, and "Gut Health impact" is bad for this user. UI 666 shows a list of weaknesses for the user. UI 668 shows a list of benefits for the user, and a list of weaknesses for this particular food along with general nutritional information.

FIG. 6K and FIG. 6L shows an example user interface for four different users eating the same food during a day along with the generated personalized scores. As can be seen, different users have different scores even though they ate the same food. As illustrated, UI 670 of FIG. 6K shows scores for a first user and UI 672 of FIG. 6K shows scores for a second user eating the same food. UI 674 of FIG. 6L shows scores for a third user and UI 676 of FIG. 6L shows scores for a fourth user eating the same food. Even though the users ate the same food, the scores for individual meals of a day as well as the scores for the day were different for the users. In certain cases additional messages are displayed for example to show the value of eating a diverse range of plants for that individual.

FIG. 6M shows nutritional guidance and scores for a user. As illustrated, UI 678 shows a day score of 37 for a user. As discussed above, the day score may be updated by the nutritional service 120 as the user eats more food. UI 680 shows the meals and foods the user has eaten within the current day, along with meal scores next to each of the meals. UI 682 shows nutritional guidance for the user indicating to add 4 portions of plants to reach a target/goal for the day. UI 684 shows nutritional guidance for the user indicating to keep an eye on their fat intake which may be triggered when fat from a previous meal has led to a lowered score for a subsequent meal or for the day as a whole.

Figure 7:
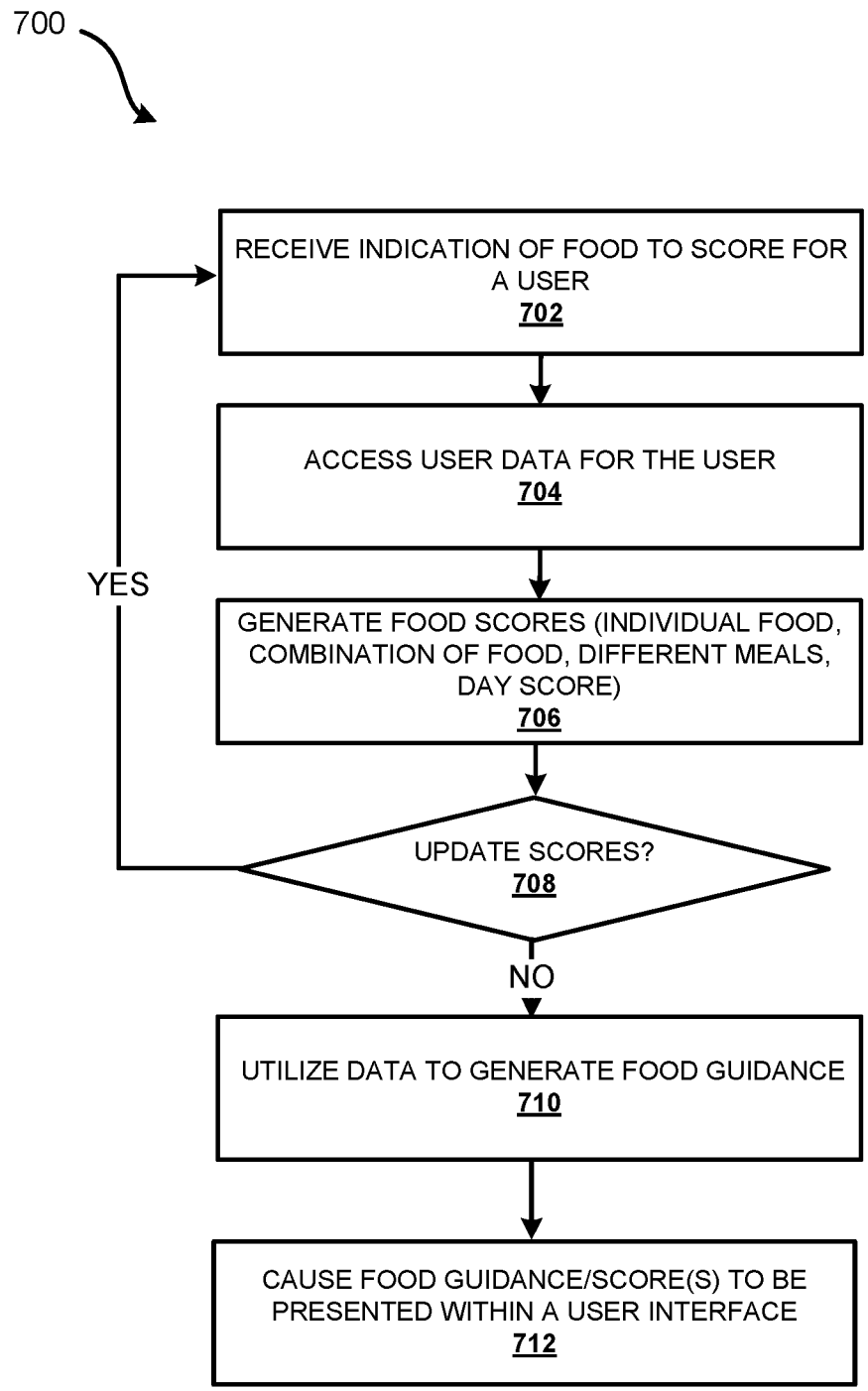
FIG. 7 is a flow diagram showing routine illustrating aspects of a mechanism disclosed herein for generating food guidance that is personalized for an individual using predicted food responses.
Figure 8:
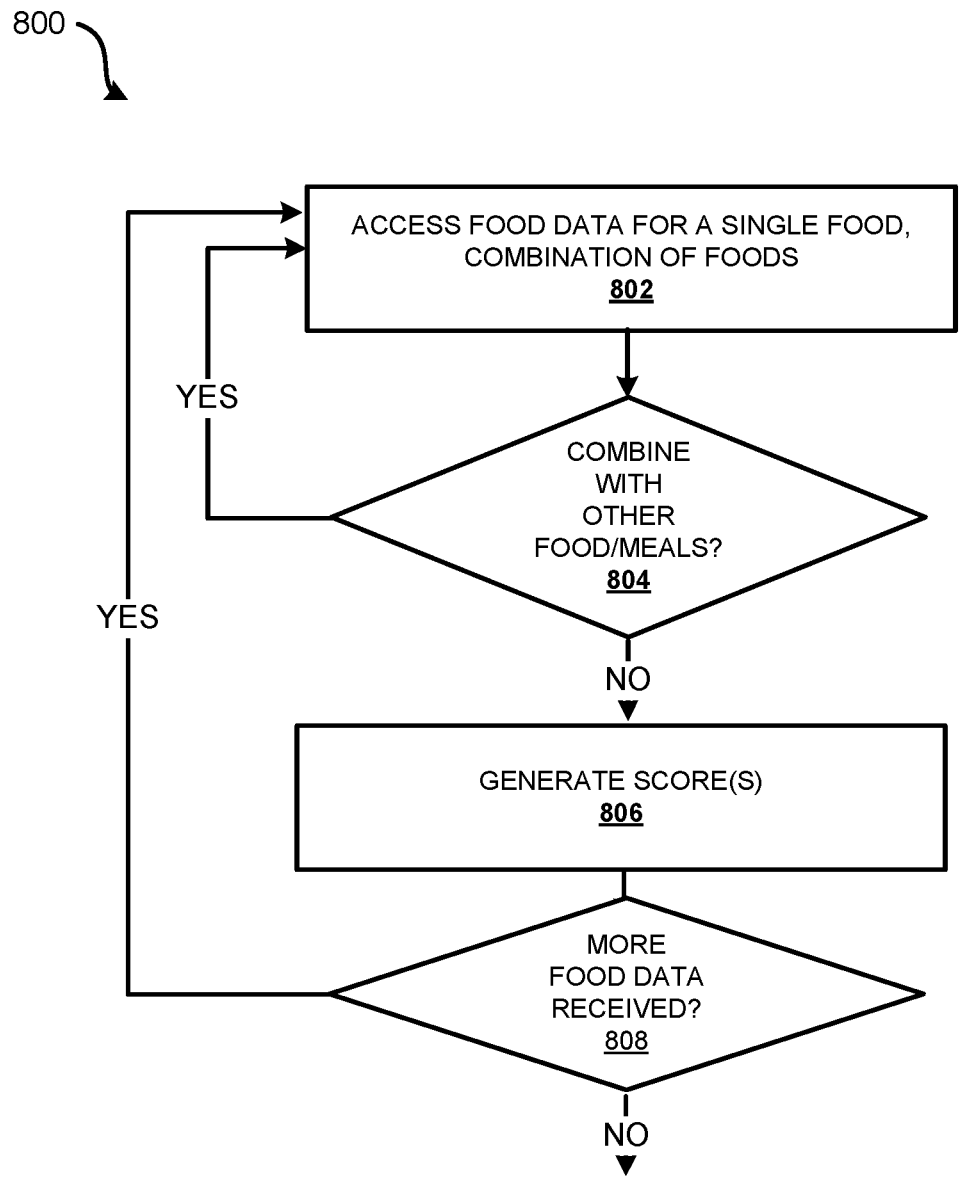
FIG. 8 is a flow diagram showing routine illustrating aspects of a mechanism disclosed herein for generating scores that are personalized for a user.

FIGS. 7 and 8 are flow diagrams showing routines 700, 800, in accordance with examples described herein. It should be appreciated that at least some of the logical operations described herein with respect to FIGS. 7 and 8, and the other FIGS., may be implemented (1) as a sequence of computer implemented acts or program modules running on a computing system and/or (2) as interconnected machine logic circuits or circuit modules within the computing system.

The implementation of the various components described herein is a matter of choice dependent on the performance and other requirements of the computing system. Accordingly, the logical operations described herein are referred to variously as operations, structural devices, acts, or modules. These operations, structural devices, acts, and modules may be implemented in software, in firmware, in special purpose digital logic and any combination thereof. It should also be appreciated that more or fewer operations may be performed than shown in the FIGS. and described herein. These operations may also be performed in parallel, or in a different order than those described herein.

FIG. 7 is a flow diagram showing routine 700 illustrating aspects of a mechanism disclosed herein for generating food guidance that is personalized for an individual using predicted food responses.

The routine 700 may begin at 702, where an indication is received for food to score for a user. As discussed above, the food can be a series of standardized meals, a single meal, a single food, or some other selection of food. In some examples, the user may provide an indication of food that has been eaten using a UI 134, or through some other mechanism. In some examples, the nutritional service 120 may provide one or more foods to score for a particular user. For instance, the nutritional service 120 may generate a list of foods based on preferences from a user, dietary restrictions, and the like.

At 704, user data for the user is accessed. As discussed above, the food guidance and scores that are generated are personalized for the user. In some configurations, the nutritional service 120 accesses data store 144 to access user data 140A. This data may be used by the nutritional service 120 to generate predictions, scores, and food guidance that is personalized for the user.

At 706, food scores are generated for the user. As discussed above, the nutritional service 120 may access one or more services to generate predictions for a response to a single food, a combination of food, as well as a combination with foods that have already been eaten by the user.

At 708, a determination is made as to whether or not to update the scores. As discussed above, the nutritional service 120 may update one or more scores throughout a time period. For example, when a day score has been calculated and more food has been eaten/scored then the nutritional service 120 may update the day score to reflect the additional food. When the scores are to be updated, the routine returns to 702. When the scores are not to be updated, the routine flows to 710.

At 710, food guidance may be generated. As discussed above, the scores that are personalized for the user and other data (e.g., user data) may be used by the nutritional service 120 to generate food guidance as illustrated above to assist the user.

At 712, the food guidance/score(s) are presented within a UI. As discussed above, the nutritional service 120 may generate UI elements to display within UI 134 such that the user may readily determine the quality/health of the food they have eaten or may eat. In some examples, the scores are presented within traffic light categories such that classification of the food as healthy, or unhealthy is readily ascertainable.

FIG. 8 is a flow diagram showing routine 800 illustrating aspects of a mechanism disclosed herein for generating scores that are personalized for a user. The routine 800 may begin at 802, where food data for a single food or combination of foods is accessed. As discussed above, the food data may include data such as nutritional content of the food, whether the food is processed, a level of food processing if the food is processed, and the like.

At 804, a determination is made as to whether to combine the food with other food/meals. As discussed above, when food is combined, a score associated with the combination of the food may change. When the food is to be combined with other food, the routine returns to 802. When the food is not to be combined, the routine flows to 806.

At 806, the scores are generated for the food. In some examples, the nutritional service 120 may use one or more machine learning mechanisms to generate the scores. The machine learning mechanisms may be trained using data obtained from experts as well as other data. In some configurations, the machine learning mechanism is trained using thousands of samples from other users. In some examples, one or more machine learning mechanisms may be used to adjust scores for a particular user.

At 804, a determination is made as to whether more food data has been received. As discussed above, when more food data is received, one or more scores may be updated and/or generated. When more food data has been received, the routine returns to 802. When more food data has been received, the routine returns to processing other actions.

Figure 9:
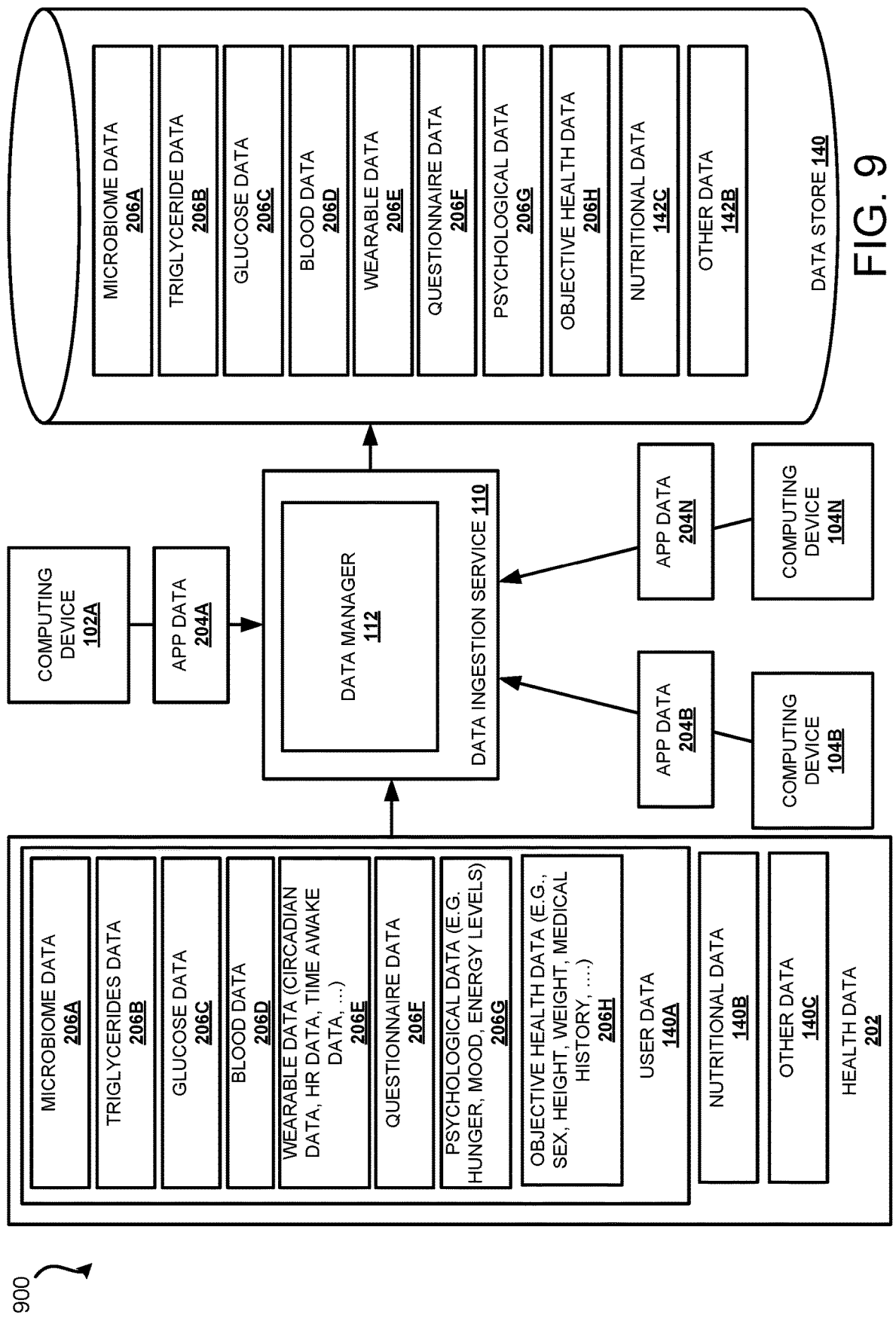
FIG. 9 is a block diagram depicting an illustrative operating environment in which a data ingestion service receives and processes data associated with data associated with at home measurements of nutritional responses.

FIG. 9 is a block diagram depicting an illustrative operating environment 900 in which a data ingestion service 110 receives and processes data associated with data associated with at home measurements of nutritional responses.

In some configurations, the data manager 112 is configured to receive data such as, health data 202 that can include, but is not limited to microbiome data 206A, triglycerides data 206B, glucose data 206C, blood data 206D, wearable data 206E that can include circadian data, questionnaire data 206F, psychological data (e.g., hunger, sleep quality, mood, . . . ) 206G, objective health data (e.g., height, weight, medical history, . . . ) 206H, nutritional data 140B, and other data 140C.

According to some examples, the microbiome data 206A includes data about the gut microbiome of an individual. The gut microbiome can host a large number of microbial species (e.g., >1000) that together have millions of genes.

The triglycerides data 206B may include data about triglycerides for an individual. In some examples, the triglycerides data 206B can be determined from an At Home Blood Test which in some cases is a finger prick on to a dried blood spot card. The glucose data 206C includes data about blood glucose. The glucose data 206C may be determined from various testing mechanisms, including at home measurements, such as a continuous glucose meter.

The blood data 206D may include blood tests relating to a variety of different biomarkers. As discussed above, at least some blood tests can be performed at home. In some configurations, the blood data 206D is associated with measuring blood sugar, insulin, c-peptides, triglycerides, cholesterol, IL-6 inflammation, ketone bodies, nutrient levels, allergy sensitivities, iron levels, blood count levels, HbA1c, and the like.

The wearable data 206E can include any data received from a computing device associated with an individual. For instance, an individual may wear an electronic data collection device 103, such as an activity-monitoring device, that monitors motion, heart rate, heart rate variability, determines how much an individual has slept that may include the types of sleep, the times an individual is awake, the number of calories burned, activities performed, blood pressure, body temperature, and the like. The individual may also wear a continuous glucose meter that monitors blood glucose levels.

The questionnaire data 206F can include data received from one or more questionnaires, and/or surveys received from one or more individuals. The psychological data 206G, that may be subjectively obtained, may include data received from the individual and/or a computing device that generates data or input based on a subjective determination (e.g., the individual states that they are still hungry after a meal, or a device estimates sleep quality based on the movement of the user at night perhaps combined with heart rate data). The objective health data 206H includes data that can be objectively measured, such as but not limited to height, weight, medical history, and the like.

The nutritional data 140B can include data about food, which is referred to herein as "food data". For example, the nutritional data can include nutritional information about different food(s) such as their macronutrients and micronutrients or the bioavailability of its nutrients under different conditions (raw vs cooked, or whole vs ground up).

The other data 142B can include other data associated with the individual. For example, the other data 142B can include data that can be received directly from a computer application that logs information for an individual (e.g., food eaten, sleep, . . . ) and/or from the user via a user interface.

In some examples, different computing devices 102 associated with different users provide application data 204 to the data manager 112 for ingestion by the data ingestion service 110. As illustrated, computing device 102A provides app data 204A to the data manager 112, computing device 104B provides app data 204B to the data manager 112, and computing device 104N provides app data 204N to the data manager 112. There may be any number of computing devices utilized.

As discussed briefly above, the data manager 112 receives data from different data sources, processes the data when needed (e.g., cleans up the data for storage in a uniform manner), and stores the data within one or more data stores, such as the data store 144.

The data manager 112 can be configured to perform processing on the data before storing the data in the data store 144. For example, the data manager 112 may receive data for ketone bodies and then use that data to generate ketone body ratios. Similarly, the data manager 112 may process food eaten and generate meal calories, number of carbohydrates, fat to carbohydrate ratios, how much fiber consumed during a time period, and the like. The data stored in the data store 144, or some other location, can be utilized by the data service 120 to determine an accuracy of at home measurements of nutritional responses performed by users. The data outputted by the data service 108B to the nutritional service may therefore contain different values than are stored in the data store 144, for example if a food quantity is adjusted.

Figure 10:
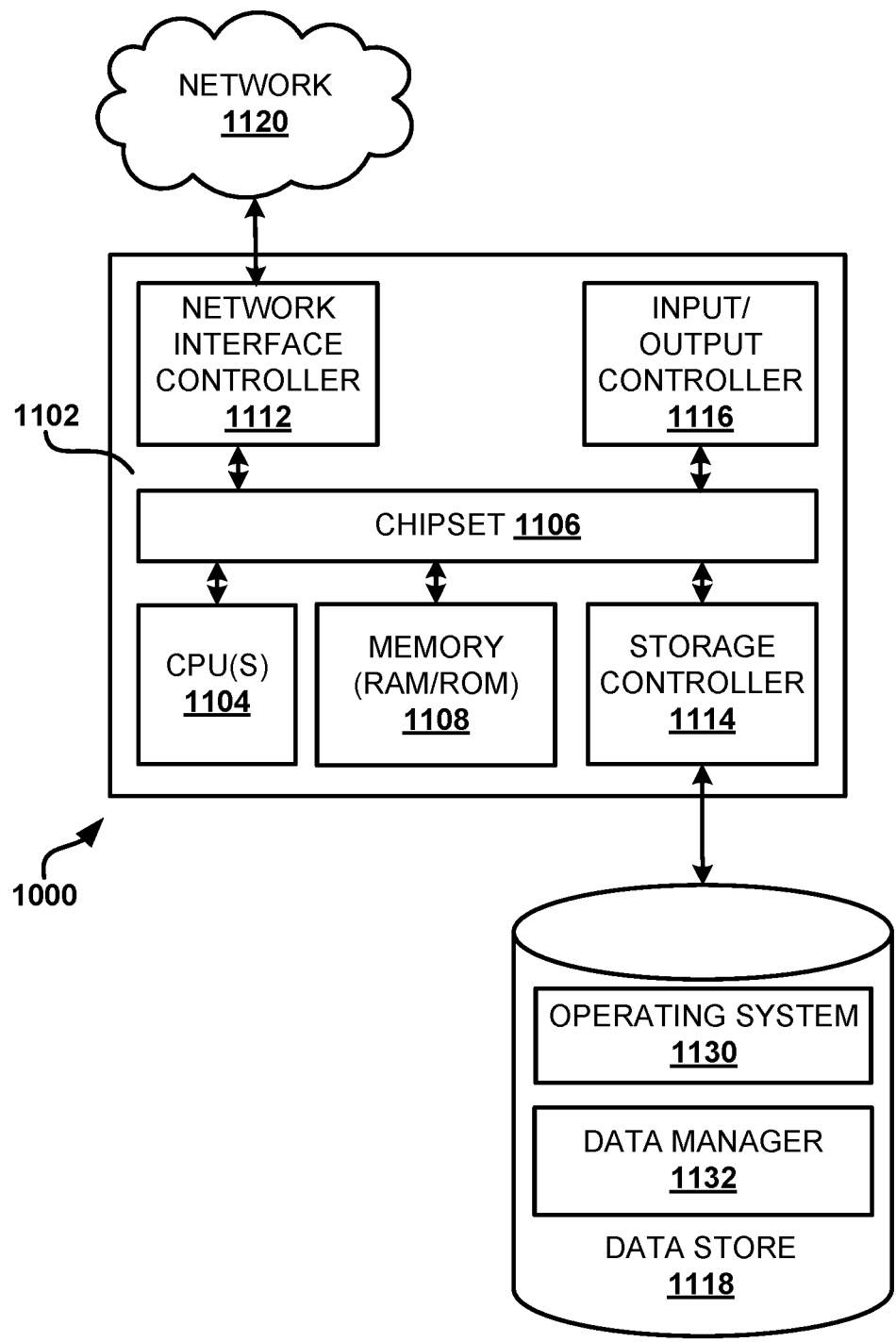
FIG. 10 is a computer architecture diagram showing one illustrative computer hardware architecture for implementing a computing device that might be utilized to implement aspects of the various examples presented herein.

FIG. 10 shows an example computer architecture for a computer 1000. The computer architecture shown in FIG. 10 illustrates a conventional server computer, workstation, desktop computer, laptop, mobile device, tablet, network appliance, digital cellular phone, smart watch, or other computing device, and may be utilized to execute any of the software components presented herein. For example, the computer architecture shown in FIG. 10 may be utilized to execute software components for performing operations as described above. The computer architecture shown in FIG. 10 might also be utilized to implement a computing device 132, or any other of the computing systems described herein.

The computer 1000 includes a baseboard 1102, or "motherboard," to which a multitude of components or devices may be connected by way of a system bus or other electrical communication paths. In one illustrative example, one or more central processing units ("CPUs") 1104 operate in conjunction with a chipset 1106. The CPUs 1104 may be standard programmable processors that perform arithmetic and logical operations necessary for the operation of the computer 1000.

The chipset 1106 provides an interface between the CPUs 1104 and the remainder of the components and devices on the baseboard 1102. The chipset 1106 may provide an interface to memory 1106, such as RAM and/or read-only memory ("ROM"). The memory may store software components utilized for the operation of the computer 1000 in accordance with the examples described herein.

The computer 1000 may operate in a networked environment using logical connections to remote computing devices and computer systems through a network, such as the network 1120. The chipset 1106 may include functionality for providing network connectivity through a network interface controller, such as a cellular network adapter, WiFi network adapter, Ethernet adapter, and the like. The NIC 1112 is capable of connecting the computer 1000 to other computing devices over the network 1120.

The computer 1000 may be connected to a mass storage device 1116 that provides storage for the computer. The mass storage device 1116 may store system programs, application programs, other program modules and data, which have been described in greater detail herein. The mass storage device 1116 may be connected to the computer 1000 through a storage controller 1114 connected to the chipset 1106. The mass storage device 1116 may consist of one or more physical storage units. The storage controller 1114 may interface with the physical storage units through various type of interfaces.

The mass storage device 1116 described above, the computer 1000 may have access to other computer-readable storage media to store and retrieve information, such as program modules, data structures, or other data. By way of example, and not limitation, computer-readable storage media may include volatile and non-volatile, removable and non-removable media implemented in any method or technology.

The mass storage device 1116 may store an operating system 1130 utilized to control the operation of the computer 1000. According to some configurations, the operating system may include, but is not limited to the UNIX operating system, the LINUX operating system, the WINDOWS® operating system from MICROSOFT Corporation, the iOS operating system from APPLE Corporation, the ANDROID operating system from GOOGLE, and the like. Other operating systems may also be utilized. The mass storage device 1116 may store other system or application programs and data utilized by the computer 1000, such as components that include the data manager 1132, and/or any of the other software components and data described above. The mass storage device 1116 might also store other programs and data not specifically identified herein.

In one example, the mass storage device 1116 or other computer-readable storage media is encoded with computer-executable instructions that, when loaded into the computer 1000, implement the examples described herein. The computer 1000 has access to computer-readable storage media storing computer-executable instructions which, when executed by the computer 1000, may be configured to perform the various routines described above. The computer 1000 might also include computer-readable storage media for performing any of the other computer-implemented operations described herein.

The computer 1000 may also include one or more input/output controllers 1116 for receiving and processing input from a number of input devices, such as an electronic data collection device, a keyboard, a mouse, a touchpad, a touch screen, an electronic stylus, or other type of input device. Similarly, the input/output controller 516 may provide output to one or more types of output devices (e.g., a display, a projector, a printer, . . . ). The computer 1000 may not include all of the components shown in FIG. 10, may include other components that are not explicitly shown in FIG. 10, or may utilize an architecture completely different than that shown in FIG. 10.

Based on the foregoing, it should be appreciated that technologies for generating food guidance using predicted food responses have been presented herein. Moreover, although some of the subject matter presented herein has been described in language specific to computer structural features, methodological acts and computer readable media, it is to be understood that the invention defined in the appended claims is not necessarily limited to the specific features, acts, or media described herein. Rather, the specific features, acts and media are disclosed as example forms of implementing at least some of the claims.

The subject matter described above is provided by way of illustration only and should not be construed as limiting. Furthermore, the claimed subject matter is not limited to implementations that solve any or all disadvantages noted in any part of this disclosure. Various modifications and changes may be made to the subject matter described herein without following the examples and applications illustrated and described, and without departing from the true spirit and scope of the present invention, which is set forth in the following claims.

What is claimed is:

1. A method, comprising:
accessing food data associated with one or more foods;
accessing first user data associated with at least a first user or users;
training, using biological measurements of the first user or users, at least a first portion of the food data associated with one or more first foods and the first user data, a first machine learning mechanism to output a plurality of predicted properties for the first user or users including at least two of:
 a first blood sugar stress prediction score associated with the one or more first foods and personalized for the first user or users,
 a first blood fats stress prediction score associated with the one or more first foods and personalized for the first user or users,
 a first gut health impact prediction score associated with the one or more first foods and personalized for the first user or users, and
 a first hunger prediction score associated with the one or more first foods and personalized for the first user or users;
training a second machine learning mechanism to output a first food score that is personalized for the first user or users, the food score based at least in part on the plurality of predicted properties for the first user or users;
accessing second user data associated with a second user;
inputting at least a second portion of the food data for one or more second foods and the second user data to the first machine learning mechanism;
receiving, from the second machine learning mechanism, a second food score that is personalized for the second user, the second food score based at least in part on the plurality of predicted properties for the second user; and causing the second food score to be presented within a user interface to the second user.

2. The method of claim 1, wherein the food data for a food indicates one or more of the food category of the food, a fat composition of the food, a fat source of the food, a fat quality of the food, a carbohydrate composition of the food, a glycemic index of the carbohydrates of the food, a carbohydrate quality of the food, a protein composition of the food, a fiber composition of the food, a level of processing of the food, a production method of the food, a user preparation method of the food, one or more flavor enhancers included in the food, one or more emulsifiers included in the food, a food preservation method of the food, a location where the food was produced, an animal method by which one or more animals contributing to the food were reared, caught, or slaughtered.

3. The method of claim 1, wherein one or more of a blood sugar control and blood fat control are calculated for the second user, reflecting a personal blood sugar response for the second user and a personal blood fats response compared against other users for the one or more second foods.

4. The method of claim 1, wherein the second food score is personalized based at least in part on a microbiome of the second user.

5. The method of claim 1, further comprising weighting the plurality of the properties for the second user based on the second user and using the weighting to generate the second food score.

6. The method of claim 1, further comprising generating the user interface, wherein generating the user interface includes generating a single food score user interface (UI) element that when presented provides a visual indication of the second food score categorized into a single category selected from categories of recommended consumption guidance, wherein the categories may be one or more of color-coded with a traffic light system, or wherein the categories for a food include two or more of a first category that indicates the food may be eaten frequently or in significant quantities, a second category that indicates that the food may be eaten regularly, a third category that indicates that the food may be eaten in moderation, and a fourth category that indicates that the food may be eaten rarely or in small quantities.

7. The method of claim 1, further comprising:
generating a blood sugar stress score for the second food that is personalized for the second user;
generating a blood fat stress score for the second food that is personalized for the second user;
generating a gut health impact score for the second food that is personalized for the second user; and
generating the user interface, wherein generating the user interface includes generating one or more of a blood sugar stress UI element that presents information associated with the blood sugar stress score, a blood fat stress UI element that presents information associated with the blood fat stress score, and a gut health impact UI element that presents information associated with the gut health impact score.

8. The method of claim 1, wherein generating the second food score is based at least in part on one or more of one or more foods previously eaten by the second user, a time of day, sleep data associated with the second user, and exercise performed by the second user.

9. The method of claim 1, further comprising generating a day score for the second user, wherein the day score is based on different food eaten during a day and can change based at least in part on at least one of the fat clearance capabilities of the second user, an amount of fat eaten throughout a time period of the day by the second user, a quality of the fat eaten throughout a time period of the day by the second user, an amount of vegetables eaten throughout the day by the second user, an amount of fruit eaten throughout the day by the second user, an amount of plants eaten throughout the day by the second user, a diversity of different plants eaten throughout the day by the second user, an amount of fiber eaten throughout the day by the second user, an amount of exercise that was performed in a previous day and/or the day, a time when exercise was done compared with when a food was eaten, and an amount/quality/timing of sleep for the second user within a specified time period.

10. The method of claim 1, wherein generating the second food score includes lowering the second food score based at least in part on determining that a number of calories exceeds a calorie threshold associated with the second user, wherein the calorie threshold is based at least in part on one or more of an activity level of the second user, a height and weight of the second user, an age of the second user, a gender of the second user, and a daily calorie usage for the second user.

11. The method of claim 1, further comprising generating food guidance for the second user, wherein the food guidance is based at least in part on the second food score, and wherein the food guidance can include targets that indicates a proportion of fat and carbohydrate for the second user to eat.

12. The method of claim 1, wherein generating the second food score is based on food that has been eaten by the second user over a time period longer than a day.

13. The method of claim 1, further comprising:
receiving an indication of food eaten by the second user at a time; and
confirming that the food was eaten by the second user at the time based at least in part on data received by an electronic device that measures a glucose response of the second user.

14. A system, comprising:
one or more processors; and
one or more computer-readable media storing computer-executable instructions that, when executed by the one or more processors, cause the one or more processors to perform acts comprising:
accessing food data associated with one or more foods;
accessing first user data associated with a first user or users;
training, using biological measurements of the first user or users, at least a first portion of the food data associated with one or more first foods and the first user data, a first machine learning mechanism to output a plurality of predicted properties for the first user or users including at least two of:
a first blood sugar stress prediction score associated with the one or more first foods and personalized for the first user or users,
a first blood fats stress prediction score associated with the one or more first foods and personalized for the first user or users,
a first gut health impact prediction score associated with the one or more first foods and personalized for the first user or users, and a first hunger prediction score associated with the one or more first foods and personalized for the first user or users;

training a second machine learning mechanism to output a first food score that is personalized for the first user or users, the food score based at least in part on the plurality of predicted properties for the first user or users;

accessing second user data associated with a second user;

inputting at least a second portion of the food data for one or more second foods and the second user data to the first machine learning mechanism;

receiving, from the first machine learning mechanism, the plurality of predicted properties for the second user;

inputting at least the plurality of predicted properties for the second user to the second machine learning mechanism;

receiving, from the second machine learning mechanism, a second food score that is personalized for the second user, the second food score based at least in part on the plurality of predicted properties for the second user; and causing the second food score to be presented within a user interface to the second user.

15. The system of claim 14, wherein the food data for a food indicates one or more of the food category of the food, a fat composition of the food, a fat source of the food, a fat quality of the food, a carbohydrate composition of the food, a glycemic index of the carbohydrates of the food, a carbohydrate quality of the food, a protein composition of the food, a fiber composition of the food, a level of processing of the food, a production method of the food, a user preparation method of the food, one or more flavor enhancers included in the food, one or more emulsifiers included in the food, a food preservation method of the food, a location where the food was produced, an animal method by which one or more animals contributing to the food were reared, caught, or slaughtered.

16. The system of claim 14, wherein one or more of a blood sugar control and blood fat control are calculated for the second user, reflecting a personal blood sugar response for the second user and a personal blood fats response compared against other users for the one or more second foods.

17. The system of claim 14, wherein the second food score is personalized based at least in part on a microbiome of the second user.

18. The system of claim 14, the acts further comprising weighting the plurality of the properties for the second user based on the second user and using the weighting to generate the second food score.

19. The system of claim 14, the acts further comprising generating the user interface, wherein generating the user interface includes generating a single food score user interface (UI) element that when presented provides a visual indication of the second food score categorized into a single category selected from categories of recommended consumption guidance, wherein the categories may be one or more of color-coded with a traffic light system, or wherein the categories for a food include two or more of a first category that indicates the food may be eaten frequently or in significant quantities, a second category that indicates that the food may be eaten regularly, a third category that indicates that the food may be eaten in moderation, and a fourth category that indicates that the food may be eaten rarely or in small quantities.

20. The system of claim 14, the acts further comprising:
generating a second blood sugar stress score for the second food that is personalized for the second user;
generating a second blood fat stress score for the second food that is personalized for the second user;
generating a second gut health impact score for the second food that is personalized for the second user; and
generating the user interface, wherein generating the user interface includes generating one or more of a blood sugar stress UI element that presents information associated with the blood sugar stress score, a blood fat stress UI element that presents information associated with the blood fat stress score, and a gut health impact UI element that presents information associated with the gut health impact score.

21. The system of claim 14, wherein generating the second food score is based at least in part on one or more of one or more foods previously eaten by the second user, a time of day, sleep data associated with the second user, and exercise performed by the second user.

22. The system of claim 14, further comprising generating a day score for the second user, wherein the day score is based on different food eaten during a day and can change based at least in part on at least one of the fat clearance capabilities of the second user, an amount of fat eaten throughout a time period of the day by the second user, a quality of the fat eaten throughout a time period of the day by the second user, an amount of vegetables eaten throughout the day by the second user, an amount of fruit eaten throughout the day by the second user, an amount of plants eaten throughout the day by the second user, a diversity of different plants eaten throughout the day by the second user, an amount of fiber eaten throughout the day by the second user, an amount of exercise that was performed in a previous day and/or the day, a time when exercise was done compared with when a food was eaten, and an amount/quality/timing of sleep for the second user within a specified time period.

23. The system of claim 14, wherein generating the second food score includes lowering the second food score based at least in part on determining that a number of calories exceeds a calorie threshold associated with the second user, wherein the calorie threshold is based at least in part on one or more of an activity level of the second user, a height and weight of the second user, an age of the second user, a gender of the second user, and a daily calorie usage for the second user.

24. The system of claim 14, further comprising generating food guidance for the second user, wherein the food guidance is based at least in part on the second food score, and wherein the food guidance can include targets that indicates a proportion of fat and carbohydrate for the second user to eat.

25. The system of claim 14, wherein generating the second food score is based on food that has been eaten by the second user over a time period longer than a day.

26. The system of claim 14, further comprising:
receiving an indication of food eaten by the second user at a time; and
confirming that the food was eaten by the second user at the time based at least in part on data received by an electronic device that measures a glucose response of the second user.

27. A non-transitory computer-readable storage medium having computer-executable instructions stored thereupon which, when executed by a computer, cause the computer to perform acts comprising:

accessing food data associated with one or more foods;

accessing first user data associated with a first user or users;

training, using biological measurements of the first user or users, at least a first portion of the food data associated with one or more first foods and the first user data, a first machine learning mechanism to output a plurality of predicted properties for the first user or users including at least two of:

a first blood sugar stress prediction score associated with the one or more first foods and personalized for the first user or users, a first blood fats stress prediction score associated with the one or more first foods and personalized or the first user or users, a first gut health impact prediction score associated with the one or more first foods and personalized for the first user or users, and a first hunger prediction score associated with the one or more first foods and personalized for the first user or users;

training a second machine learning mechanism to output a first food score that is personalized for the first user or users, the food score based at least in part on the plurality of predicted properties for the first user or users;

accessing second user data associated with a second user;

inputting at least a second portion of the food data for one or more second foods and the second user data to the first machine learning mechanism;

receiving, from the first machine learning mechanism, the plurality of predicted properties for the second user;

inputting at least the plurality of predicted properties for the second user to the second machine learning mechanism;

receiving, from the second machine learning mechanism, a second food score that is personalized for the second user, the second food score based at last in part on the plurality of predicted proper ties for the second user; and causing the second food score to be presented within a user interface to the second user.

28. The non-transitory computer-readable storage medium of claim 27, wherein the food data for a food indicates one or more of the food category of the food, a fat composition of the food, a fat source of the food, a fat quality of the food, a carbohydrate composition of the food, a glycemic index of the carbohydrates of the food, a carbohydrate quality of the food, a protein composition of the food, a fiber composition of the food, a level of processing of the food, a production method of the food, a user preparation method of the food, one or more flavor enhancers included in the food, one or more emulsifiers included in the food, a food preservation method of the food, a location where the food was produced, an animal method by which one or more animals contributing to the food were reared, caught, or slaughtered.

\* \* \* \* \*